(12) United States Patent
Dieker et al.

(10) Patent No.: US 11,600,190 B2
(45) Date of Patent: *Mar. 7, 2023

(54) SIMULATION THERAPY FOR AUTISM SPECTRUM DISORDER

(71) Applicant: University of Central Florida Research Foundation, Inc., Orlando, FL (US)

(72) Inventors: Lisa A. Dieker, Orlando, FL (US); Michael Hynes, Orlando, FL (US); Charles Hughes, Orlando, FL (US); Eleazar Vasquez, Orlando, FL (US); Kathleen Ingraham, Orlando, FL (US); Claire Donehower Paul, Orlando, FL (US); Taylor Bousfield, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/887,673

(22) Filed: Aug. 15, 2022

(65) Prior Publication Data

US 2022/0392363 A1 Dec. 8, 2022

Related U.S. Application Data

(63) Continuation of application No. 17/670,668, filed on Feb. 14, 2022, now Pat. No. 11,450,220, which is a
(Continued)

(51) Int. Cl.
*G09B 5/06* (2006.01)
*G09B 19/00* (2006.01)
(Continued)

(52) U.S. Cl.
CPC ............. *G09B 5/06* (2013.01); *G06F 9/3877* (2013.01); *G06T 15/00* (2013.01); *G06T 15/005* (2013.01);
(Continued)

(58) Field of Classification Search
CPC .......... G09B 5/06; G06T 15/00; G06V 40/10
See application file for complete search history.

(56) References Cited

U.S. PATENT DOCUMENTS

| 10,783,800 B1 * | 9/2020 | Dieker ................... G06V 40/10 |
| 2008/0071136 A1 * | 3/2008 | Oohashi ................... G10H 7/00 600/27 |

* cited by examiner

*Primary Examiner* — Robert J Utama
(74) *Attorney, Agent, or Firm* — Anton J. Hopen; Smith & Hopen, P.A.

(57) ABSTRACT

An adaptive computer simulation rendering system is disclosed for conditioning an individual having Autism Spectrum Disorder (ASD) to real-world environments through variable sensory output in computer simulations. The subject is fully or partially immersed in a computer-simulated environment for a time-limited session. Real-time monitoring of the human subject is performed for a change in a sensor-derived, quantified sensory load level. Responsive to an increase in sensory load level, the computer-simulated environment modulates the sensor load on the individual. The human subject adapts to increasingly complex environments by this modulation of simulation thereby providing therapeutic benefit to the individual with ASD.

20 Claims, 22 Drawing Sheets

Related U.S. Application Data continuation of application No. 16/997,404, filed on Aug. 19, 2020, now Pat. No. 11,282,403, which is a continuation of application No. 16/801,333, filed on Feb. 26, 2020, now Pat. No. 10,783,800.

(51) Int. Cl.
*G06T 15/00* (2011.01)
*G06F 9/38* (2018.01)
*G06V 20/20* (2022.01)
*G06V 40/10* (2022.01)
*G06V 40/16* (2022.01)

(52) U.S. Cl.
CPC .............. *G06V 20/20* (2022.01); *G06V 40/10* (2022.01); *G06V 40/161* (2022.01); *G09B 19/00* (2013.01); *G06T 2215/16* (2013.01)

SIMULATION THERAPY FOR AUTISM SPECTRUM DISORDER

CROSS REFERENCE TO RELATED APPLICATIONS

This application is a continuation of and claims priority U.S. Non-Provisional patent application Ser. No. 17/670,668, entitled "Adaptive Simulation Rendering on Sensory Load", filed on Feb. 14, 2022 which claims priority to U.S. Non-Provisional patent application Ser. No. 16/997,404 (now U.S. Pat. No. 11,282,403), entitled "Physiologic Responsive Rendering of Computer Simulation", filed on Aug. 19, 2020, which claims priority to U.S. Non-Provisional patent application Ser. No. 16/801,333 (now U.S. Pat. No. 10,783,800), entitled "Sensor-Based Complexity Modulation for Therapeutic Computer-Simulations", filed on Feb. 26, 2020, the contents of which are herein incorporated by reference.

BACKGROUND OF THE INVENTION

1. Field of the Invention

This invention relates to modulate an immersive computer simulation for individuals on the autism spectrum responsive to physiologic data indicative of the sensory load the computer simulation has on the individual.

2. Brief Description of the Related Art

The Center for Disease Control currently reports the rise in the number of students with Autism Spectrum Disorder (ASD) to be of epidemic proportions. Despite numerous curricula being developed to support individuals with ASD, none employs virtual environment context that can provide skills in EF using approximations of practice aligned with the individual's real life. Despite the increased diagnosis of ASD, existing technologies are not well-aligned to provide a safe, nimble, scaffolded stimulation, and personalized practice space for those with ASD to master critical skills.

Research and inventions for individuals with ASD learning social/emotional and communication skills (EF) through a virtual environment does not currently exist. Although "human-to-human-based" training has value for those with ASD, this methodology has been shown in practice to be not effective and to create anxiety. Research in video modeling has been proven effective, and this work enhances or supplements past success in using video models in an immersive virtual environment.

ASD is just one example of a condition that is exacerbated by sensory overload. Sensory overload has been found to be associated with other disorders and conditions such as schizophrenia, Tourette syndrome, attention deficit hyperactivity disorder (ADHD), obsessive-compulsive disorder (OCD), attention deficit disorder (ADD), emotional behavioral disorders (EBD), and post-traumatic stress disorder (PTSD). General symptoms include irritability; over-sensitivity to movement, sights, sounds or touch; difficulty with social interactions; muscle tension; outbursts; difficulty making eye contact; overexcitement; repeatedly changing activities without completing tasks; hyperhidrosis; and restlessness.

Sensory overload is often addressed by participation in occupational therapy, outright avoidance, or limiting of environmental stimuli. Unfortunately, common environmental elements are nearly impossible to evade, including mass media, urbanization, crowding, digital immersion technologies, and ambient noise. For many young individuals, students, adults, and military veterans suffering from conditions related to sensory overload, limiting interactions with sources of impacting stimuli may not be an option when furthering educational, career and social objectives. What is needed is a way to adapt a simulated environment to the sensory thresholds of each individual to develop executive functions without overstimulation of the individual or under-challenging the individual's capabilities.

BRIEF SUMMARY OF THE INVENTION

The long-standing but heretofore unfulfilled need for EF development is now met by a new, useful, and nonobvious invention. This intervention replicates interactions in a controlled environment found to transfer EF skills back into the home, school, and community life of individuals having conditions such as ASD, PTSD, and ADD to name a few. Specific objectives are set in the environment with computer-automated avatars interacting in a controlled setting to work on the development of EF skills. For work in EF this allows for controlled and repeated practice, which has been found to impact communication skills of students with ASD.

With the report by the CDC that 1 in 59 children are on the ASD spectrum, this complex yet adaptable system provides a safe and effective tool to work on targeted skills in EF. This virtual environment allows for students with sensory overload, including ASD who may be anxious about a situation to experience the situation and work on EF prior to the real-world situation (e.g., doctor's visit, asking out a peer on a date, asking for help in a situation).

Throughout a series of treatments for a student, the scenarios are customized through visual access to the students with sensory overload, including ASD and by the AI using machine learning techniques to select behaviors based on a variety of observations including facial expressions, body poses, vocalizations, and verbalizations. Beyond the customized setting, the system can personalize the level of verbal interaction and social-emotional situations experienced to provide for repeated practice of EF skills. The intensity of the scenario can be escalated or de-escalated depending on the objective, tolerance, and the desired outcome specified by the intervention team aligned with learning versus mastering an EF skill. Sensitive topics such as sexual assault, personal hygiene, or dating can be addressed along with more simplistic topics such as talking with a peer in a group to basic communication skills for employment or self-sufficiency.

When a student with sensory overload, including ASD, first steps into the simulator, familiarization with the selected environment is established. The targeted EF can be practiced over and over again until a desired level of mastery is reached and sustained. Target areas that are not met can be re-adjusted unlike in a traditional game-based situation that requires writing new code or role-play that results in subject fatigue. This virtual system can achieve a scaffolded level of response to obtaining EF skills.

An embodiment of the invention includes an apparatus for a therapeutic treatment of a human subject with environmental anxiety disorder. The apparatus generally consists of sensors, video displays, computer processor, and memory storage devices. A control module comprising a computer processor is communicatively coupled to a simulation data store, the simulation data store has machine-readable values for computer-generated features in a computer-simulated environment in which the human subject is immersed and tasked to perform an executive function. The executive function for a child could be simply stacking blocks. An executive function for an autistic adult could be cooking a simple meal in a kitchen. A common characteristic of the executive function assigned is that a sufficient increase in anxiety state by the human subject hinders successful completion of the executive function. For example, a child may become anxious when surrounded by two or more adults, subject to loud ambient noise and/or when immersed into a harshly lit environment. All these features of the real world that impact the child's ability to function and perform common tasks can be simulated and adjusted dynamically in a computer-simulated environment.

In this embodiment of the invention, the computer-generated features include visual objects and an audio output. The visual objects could be two-dimensional or three-dimensional, and the audio output could be single or multi-channel (e.g., spatial "surround sound"). A rendering module is communicatively coupled to the control module. The rendering module is further communicatively coupled to a graphic processing unit (GPU) that generates the visual objects in the computer-simulated environment through a visual display device.

The visual display device is communicatively coupled to the rendering module and the GPU, the visual display device displaying the visual objects in the computer-simulated environment. The visual display device may include single panel display monitors, multi-panel display monitors, rear projection displays, front projection displays, head-mounted virtual reality displays, and head-mounted augmented reality displays. An audio processing unit (APU) is communicatively coupled to the rendering module, and the APU generates the audio output in the computer-simulated environment in single or multiple audio channels.

An array of sensory variables is accessible by the rendering module, the sensory variables quantify an amount of visual and audible information generated by the rendering module and presented in the computer-simulated environment. The sensory variables may include audible noise, audio volume, quantity of visual objects in the environment, movement of visual objects in the environment, polygon count of rendered objects in the environment, lighting complexity of the environment, texture complexity of rendered objects in the environment, and rendered frames-per-second.

Communicatively coupled to the control module is a sensing module. Further communicatively coupled to the sensing module are at least one or more digital sensors, including cameras, radar, thermometers, heart rate monitor, pulse-oximeters and microphones. The sensing module receives non-transitory data signals from the digital sensors indicative of a physiological parameter of the human subject From data received from the sensing module, a real-time anxiety value of the human subject is derived from the data signals indicative of the physiological parameter, the real-time anxiety value readable by the control module. By way of example, a common physiological parameter may be heart rate. This can be read by a pulse meter or pulse-oximeter directly affixed to the human subject. Alternatively, it may be read remotely by radar, ultrasonic sensor or other means known in the art of pulse rate acquisition.

An anxiety threshold datastore is communicatively coupled to the control module, the anxiety threshold datastore stores an upper anxiety state value constant representing a physiological diminished capability of performing executive functions and a lower anxiety state value constant associated with a sufficiently low physiological anxiety state whereby executive functions may be successfully performed with additional stress-induced anxiety, the upper anxiety state value and the lower anxiety state value computed by one or more quantitative factors selected from the group consisting of pulse rate, respiration rate, skin temperature, and diaphoresis.

An anxiety threshold function is operable on the control module, the anxiety threshold function receiving the real-time anxiety value of the human subject, the upper anxiety value constant and the lower anxiety value constant whereby the anxiety threshold function returns a low result responsive to the real-time anxiety value of the human subject being less than the lower anxiety value; a high result responsive to the real-time anxiety value of the human subject being greater than the upper anxiety value; and an inbounds result responsive to the real-time anxiety value of the human subject being above the lower anxiety value and less than the upper anxiety value.

Responsive to a low result returned from the anxiety threshold function, the control module instructs the rendering module to increase the values of the sensory variables to thereby increase the amount of visual and audible information generated (e.g., simulation complexity) by the rendering module and presented within the computer-simulated environment Responsive to a high result returned from the anxiety threshold function, the control module instructs the rendering module to decrease the values of the sensory variables to thereby decrease the amount of visual and audible information generated by the rendering module and presented within the computer-simulated environment Finally, responsive to an inbounds result returned from the anxiety threshold function, the control module instructs the rendering module to maintain substantially the same values of the sensory variables to thereby sustain the same amount of visual and audible information generated by the rendering module and presented within the computer-simulated environment.

The human subject therapeutically develops proficiency in the executive function through the use of the apparatus by optimizing the amount of visual and audible information presented within the computer-simulated environment to sufficiently challenge the human subject by increasing visual and audible information rendered in the computer-simulated environment without detrimentally overloading the human subject with excessive visual and audible information.

An embodiment of the invention includes a method of developing executive functions for a human subject having an anxiety disorder in a computer-simulated environment. The method includes establishing a baseline anxiety level for the human subject wherein the baseline is assessed by automatically monitoring the phenotypic anxiety level of the human subject by one or more computer coupled sensors. The baseline may be obtained prior to the start of the computer simulation or within a computer simulation that is relatively "idle" without significant interaction or tasks assigned to the human subject Once the baseline anxiety level is obtained, the human subject is tasked with an executive function wherein the human subject is fully or partially immersed in the computer-simulated environment for a time-limited session.

Executive function is often considered an umbrella term for the neurologically-based skills involving mental control and self-regulation. Executive functions include task initiation, impulse control, self-monitoring, emotional control, flexible thinking, working memory, planning, and organization. Accordingly, for a young child, stacking of blocks may involve several executive functions that may be impacted by environmental stimuli. In the case of a computer-simulated environment, the child (the human subject) may have trouble performing this task during preschool with other children, teachers, ambient noises, lighting, smells, and visual complexity. Accordingly, for that child, a virtual schoolroom may be the computer-simulated environment wherein the intensity of the sensory experience may be controlled.

In yet another example, a military veteran who has combat-induced PTSD may have trouble performing executive functions related to a manufacturing job wherein sounds, vibrations and visuals may cause anxiety that detracts from her ability to perform her job. In such a case, the executive function task monitored during the computer-simulated environment may be assembling a wiring harness for a robotic arm. As needed, the tasks may be generic but related to specific objectives such as manual dexterity, memory retention, organization, and prioritization. Alternatively, they may also be specific to certain occupations, educational objectives, or even competitive sports.

In yet another example, a young professional soccer player exhibits a high level of play during practice but suffers during matches in large stadiums. The executive function in this scenario may be his ability to control the ball, and the computer-simulated environment may be that of a large stadium during a World Cup match. His anxiety level may be impacted by the ambient noise of the stadium or even responsive to fans from the opposing team heckling him. In such an application, the subject may be immersed in an augmented reality environment wherein the stadium visuals and noise exist in combination with a trainer engaged in drills with the subject. In the soccer embodiment (and applicable to others), the frame rate of the rendered simulation may be adjusted. Particularly for simulations with fast-moving elements, the frame rate may be increased from 30 to 60 to even 120 frames per second or above (subject to the limitations of the display device). For example, MICROSOFT CORPORATION publishes target frame rates of his HOLOLEN product at 60 frames per second. For hardware branded WINDOWS MIXED REALITY PCs the target frame rate is 60 frames per second. For hardware branded WINDOWS MIXED REALITY ULTRA PCs, the target framerate is 90 frames per second.

Additional computer-generated environments may include, but are not limited to, battlefield simulations for military personnel training, classroom environments for students and instructors, vehicle simulations for driving and flight training, aircraft simulations for flight anxiety therapy, hospital simulations for training for medical personnel and workplace simulations for career and vocational training. It is important to note that the physiological monitoring and modulation of the computer-simulated environmental complexity of this invention does not make the executive function more difficult or easier (e.g., modifying the difficulty level of a game). Rather, the apparatus modifies the sensory complexity of the computer simulation. It is the anxiety-reactive stimulation modulation of an individual undergoing therapy that enables prolonged sessions and engagement by the individual in an increasingly complex and realistic environment. The digital sensors react more consistently and quickly than is possible by human observation to acclimate the computer-simulated environment to the capabilities and tolerance of the treated individual.

The human visual system can process between 10 and 12 images per second and perceive them individually, while higher rates are perceived as motion. Higher frame rates for fast-moving computer-simulated environments produce a more intense sensory experience. Therefore, responsive to sensor-detected elevated anxiety levels, frame rates may be reduced in the simulation.

In yet another application of the invention, an individual suffering from flying anxiety may be immersed in a virtual, augmented, or mixed reality environment simulating the cabin of a commercial aircraft. In an embodiment of the invention, the computer simulation may also include vibrations and tilting of the subject's chair to simulate takeoffs, landings, and turbulence. The computer simulation can modify the intensity of the simulation by controlling the number of passengers (typically automated avatars), the behaviors of the passengers (e.g., belligerent passengers, crying children, sleeping passengers), ambient noise levels, dialog loops of the automated avatars, and the like. The subject's phenotypic anxiety level (e.g., pulse, temperature, facial expressions, etc. . . . ) automatically modifies the simulation within a threshold that maintains a therapeutic benefit to the subject without overwhelming the subject. The phenotypical anxiety level detected by sensors may anticipate the conscious anxiety of the subject so that the computer simulation reacts faster than a subject or human observer could under manual control.

The human subject is automatically monitored in real-time for a change in phenotypic anxiety level by the one or more computer coupled sensors. The sensor may include cameras to monitor facial expressions, body movement, and eye movement. An infrared, remote thermometer may measure body temperature. A pulse-oximeter may measure pulse rate. A microphone measures speech patterns and the volume in which the human subject speaks.

Responsive to an increase in the sensor-detected anxiety level, a computer coupled to the sensor and coupled as well to the computer-simulated environment decreases the sensory complexity of one or more features of the computer-simulated environment. The features of the computer-simulated environment may include audible noise, audio volume, quantity of visual objects in the environment, movement of visual objects in the environment, polygon count of rendered objects in the environment, lighting complexity of rendered objects in the environment, texture complexity of rendered objects in the environment, olfactory dispersions, tactile feedback frequency to the human subject, tactile feedback intensity to the human subject, frames per second rendered and simulation event repetition. Responsive to a decrease in the sensor-detected anxiety level, the computer automatically reintroduces sensory complexity to the computer-simulated environment wherein the human subject therapeutically develops proficiency in executive functions in increasingly complex environments.

Where a plurality of phenotypic anxiety levels are obtained through the sensors, they may each be normalized to a proportion of overall subject anxiety and aggregated to a total anxiety level value wherein a baseline anxiety level is dynamically linked to a median level of computer-simulated environment complexity. For example, a rise in pulse rate by 20 beats per minute may be weighted more heavily that a 4 decibel rise in the subject's speech volume.

A threshold total anxiety level value may be calculated. When such value is reached the computer automatically reduces computer-simulated environment complexity. The threshold total anxiety level may be higher or lower than the baseline wherein simulation complexity does not immediately increase or decrease until the threshold value is reached. For example, if a baseline anxiety level of 50 is calculated prior to the start of the simulation, increases in simulation complexity do not initiate until the threshold falls under a value of 40, nor do decreases in simulation complexity or until the threshold anxiety level of 60 is reached.

The computer-simulated environmental complexity applied by the computer may be inversely related to the sensor-detected total anxiety level whereby lower total anxiety levels cause the computer to increase computer-simulated environmental complexity and higher total anxiety levels cause the computer to decrease computer-simulated environmental complexity. The computer-simulated environment may be initiated at a low complexity upon initiation of the session and incrementally increased over the session until a threshold anxiety level is reached, at which time the computer either maintains or reduces the complexity of the computer-simulated environment.

In an embodiment of the invention, an executive function evaluation apparatus is introduced providing real-time quantitative values on the competency of the patient performing the executive function wherein the computer automatically adjusts the complexity of the computer-simulated environment responsive to the executive function competency (exclusively or in association with the sensor data) wherein higher levels of detected competency increase complexity of the computer-simulated environment and lower levels of detected competency decrease the complexity of the computer-simulated environment. The executive function evaluation apparatus may measure dexterity with physical objects. This could be as simple as detecting through mechanical means involving the insertion of a round peg into a round hole or a cube into a square opening. The apparatus may be more complex measuring the dexterity of the human subject with a wireless device containing accelerometers that communicate orientation responsive to directives of the computer-simulated environment (e.g., point to an object).

Alternatively, the executive function evaluation apparatus measures comprehension of the information presented in the computer simulated environment by the movement of physical objects such as an ordering or arranging tasks. In yet another embodiment of the invention, the executive function evaluation apparatus measures comprehension by entries on a computing device responsive to prompts presented in the computer-simulated environment. The computing device may be a keyboard, touchscreen or one detecting gestures via motion-capture.

In an embodiment of the invention, the computer-simulated environment has at least one avatar. The avatar may be automated, responding to predefined actions by the human subject. In yet another embodiment of the invention, a plurality of avatars may be presented in the computer-simulated environment Additionally, automated avatars may serve as "extras" in the simulation to incrementally increase simulation complexity. An embodiment of the invention automatically controls certain aspects of the avatar to challenge the subject or lessen anxiety on the subject as determinedly the sensor-detected anxiety level of the subject. For example, the aggressiveness of the posture and poses an avatar takes may increase anxiety but may also be useful in training a subject for real-world experiences. The avatar's facial expressions, voice pitch, timbre, and volume may all be automatically or partially controlled responsive to the anxiety state of the subject undergoing therapy. For example, a subject interacting with an "anti-bully" simulation may learn to control their response to anxiety-prone situations which is monitored by their pulse, body temperature and other sensor-detectable biometrics. The avatar could also be an animal. For example, an individual that suffers from anxiety responsive to interactions with dogs might find the avatar representation of a dog calms in direct relation to the subject's ability to low her anxiety level determined by her sensor-detected pulse and facial expressions. Specifically, the dog has several "micro-poses" that show different states of emotion including friendly, scared, angry and relaxed.

In addition to a method, the present invention includes an apparatus embodiment which incorporates a computing device, a plurality of sensors coupled to the computing device, the sensors establishing a baseline anxiety level for the human subject, and the baseline assessed by automatically monitoring the phenotypic anxiety level of the human subject A projection device is communicatively coupled to the computing device; the projection device displays the computer-simulated environment to the human subject. The projection device may include single panel display monitors, multi-panel display monitors, rear projection displays, front projection displays, head-mounted virtual reality displays, and head-mounted augmented reality displays.

An executive function monitoring apparatus is communicatively coupled to the computing device, and the monitoring apparatus quantifies the competency of the human subject to perform one or more executive functions while immersed in the computer-simulated environment. An avatar module is communicatively coupled to the computing device; the avatar module causes an avatar to appear within the computer-simulated environment and interact with the human subject. An anxiety level module is communicatively coupled to the computing device; the anxiety level module automatically monitors, in real-time, the human subject for a change in anxiety level by the one or more computer coupled sensors. A simulation complexity module is communicatively coupled to the computing device; the simulation complexity module responds to an increase in the sensor-detected anxiety level by decreasing the sensory complexity of one or more features of the computer-simulated environment. Similarly, the simulation complexity module responds to a decrease in the sensor-detected anxiety level by automatically reintroducing sensory complexity to the computer-simulated environment, wherein the human subject therapeutically develops proficiency in executive functions in increasingly complex environments.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
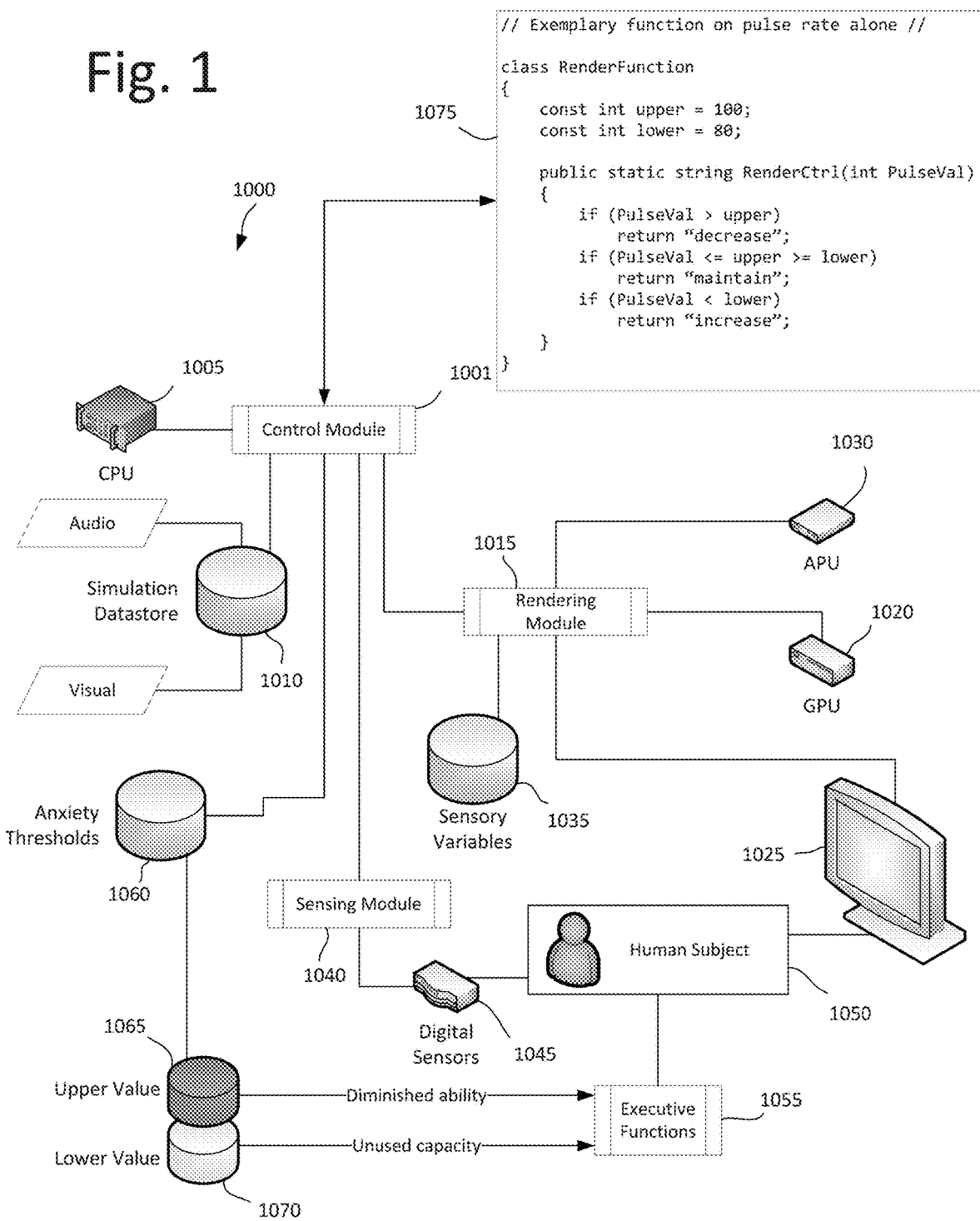
FIG. 1 is a diagrammatic view of an embodiment of the invention comprising computer components and software modules having computer-readable instructions stored in computer-readable memory executed by a computer processor.

Turning to FIG. 1, the apparatus is denoted a reference number 1000 as a whole. Control module 1001 includes computer processing unit 1005 that executes functions, procedures and routines embodied on non-transitory computer media. Control module 1001 is communicatively coupled to simulation datastore 1010 which is a repository for computer-generated features in a computer-simulated environment. The computer-generated features may include background structures, landscapes, and static views. The computer-generated features may also include static and moving objects to which the human subject 1050, immersed in the virtual computer-simulated environment engages with. Within the environment, the human subject 1050 is tasked to perform an executive function. This executive function requires a sufficient level of cognitive function whereby an increase in the anxiety state of the human subject 1050 would hinder the successful completion of the executive function.

It should be noted that the executive function may span a spectrum from simple object manipulation, public speaking to athletic performance. For example, an executive function could be a soccer player taking a penalty kick to determine the outcome of the World Cup. The human subject in this example could be placed in a room having simulated turf, a ball, and a net. The computer simulation could be rendered to a head-mounted augmented reality display (HMD) wherein the physically present ball can be kicked but a capacity-filled soccer stadium is rendered in 360 degrees onto the HMD worn by the human subject. The computer simulation renders the spectators, opposing players and loud, ambient noise of the cheering stadium to acclimate the human subject to simulate the stress and anxiety of the situation. At some point, a sufficient level of anxiety imparted on the human subject would hinder his or her ability to competently kick the ball into the net to score the penalty shot. In the parlance of sports, the human subject would "choke" and shoot poorly.

Returning back to FIG. 1, a rendering module 1015 is communicatively coupled to the control module 1001. The rendering module is further communicatively coupled to a graphic processing unit (GPU) 1020 that generates the visual objects in the computer-simulated environment A visual display device 1025 is communicatively coupled to the rendering module 1015 and the GPU 1020. In the example above, it might be the augmented reality HMD, such as those sold under the brand HOLOLENS by Microsoft Corporation. Alternatively, the display device 1025 maybe single panel display monitors, groups of displays forming multi-panel display monitors, rear projection displays, front projection displays and virtual reality HMDs. These technologies provide different levels of realism and immersion into the computer-simulated environment.

Also coupled communicatively to the rendering module is an audio processing unit (APU) 1030, which generates audio output in the computer-simulated environment. This may include but is not limited to, background noise, background dialog, foreground dialog, and foreground noise. The APU 1030 may generate audio that is spatially coordinated with visual objects rendered through the GPU 1020. For example, an indiscernible background conversation forming ambient noise may be spatially aligned with a GPU 1020 rendered of two individuals off in a distance conversing.

An array of sensory variables 1035 is made accessible to the rendering module 1015. The sensory variables 1035 quantify an amount of visual and audible information generated by the rendering module 1015 and presented in the computer-simulated environment. As they are variables, they are subject to modification in line with the objectives of the present invention. The values can be increased or decreased automatically. These sensory variables 1035 may include audible noise, audio volume, quantity of visual objects in the environment, movement of visual objects in the environment, polygon count of rendered objects in the environment, lighting complexity of the environment, texture complexity of rendered objects in the environment, and rendered frames-per-second.

For example, in the case of audible noise, the variable could relate to the frequency in which a bird chirps in the background. A low value would be an interval of once per minute. A relatively higher value would be twenty (20) times per minute. In the case of quantity of visual objects in the environment, a desk may be cluttered with pencils, staplers, tape, paper, computer peripherals and the like. For certain human subjects, a reduction of this clutter (by reducing the quantity of visual objects) reduces anxiety levels. For a computer-simulated environment wherein the executive function task is to cross a busy street, the movement of the vehicles (rendered objects) up and down the street may be automatically slowed or increased. Harsh or complex lighting may be imposed or reduced by adjusting the quantity of rendered light sources, the light intensity, the diffusion of the shadows, and the distance of the light source to objects. Texture complexity may relate to the realism of the computer-simulated environment. The texture complexity may be simplified or rendered in softer materials to mitigate anxious responses by the human subject Frames per second rendered by the display device may be used to mitigate or induce anxiety in some subjects whereby high frame rates may be associated with more dynamic and action-based environments while slower frame rates may be considered more soothing.

A sensing module 1040 is provided and communicatively coupled to the control module 1001. Coupled to the sensing module 1040 are at least one or more digital sensors 1045 including cameras, radar, thermometers, heart rate monitor, pulse-oximeters, capacitive skin monitors and microphones. The sensing module 1040 receives non-transitory data signals from the digital sensors 1045 indicative of a physiological parameter of the human subject 1050. This physiological parameter may include but is not limited to, pulse rate, oxygen levels, body temperature, body movement, body pose, speech patterns, speech volume, perspiration, and the like. A real-time anxiety value of the human subject 1050 is quantified from the data signals indicative of the physiological parameter wherein the real-time anxiety value is readable by the control module 1001.

An anxiety threshold datastore 1060 is communicatively coupled to the control module 1001. The anxiety threshold datastore 1060 stores an upper anxiety state value constant 1065 representing a diminished physiological capability of performing executive functions. A lower anxiety state value constant 1070 is associated with a sufficiently low physiological anxiety state whereby executive functions may be successfully performed with additional stress-induced anxiety. The upper anxiety state value constant 1065 and the lower anxiety state value constant 1070 are computed by one or more quantitative factors selected including, but not limited to, pulse rate, oxygen level, respiration rate, skin temperature and diaphoresis.

An anxiety threshold function 1075 operable on the control module 1001 is provided. The anxiety threshold function 1075 receives a real-time anxiety value of the human subject, the upper anxiety value constant, and the lower anxiety value constant. The anxiety threshold function 1075 returns a low result responsive to the real-time anxiety value of the human subject being less than the lower anxiety value. The function 1075 returns a high result responsive to the real-time anxiety value of the human subject being greater than the upper anxiety value. Finally, the function 1075 returns an inbounds result responsive to the real-time anxiety value of the human subject being above the lower anxiety value and less than the upper anxiety value.

Responsive to a low result returned from the anxiety threshold function 1075, the control module 1001 instructs the rendering module 1015 to increase the values of the sensory variables 1035 to thereby increase the amount of visual and audible information generated by the rendering module 1015 and presented within the computer-simulated environment Responsive to a high result returned from the anxiety threshold function 1075, the control module 1001 instructs the rendering module 1015 to decrease the values of the sensory variables 1035 to thereby decrease the amount of visual and audible information generated by the rendering module 1015 and presented within the computer-simulated environment Finally, responsive to an inbounds result returned from the anxiety threshold function 1075, the control module 1001 instructs the rendering module 1015 to maintain substantially the same values of the sensory variables 1035 to thereby sustain the same amount of visual and audible information generated by the rendering module 1015 and presented within the computer-simulated environment.

The human subject 1050 therapeutically develops proficiency in the executive function 1055 by optimizing the amount of visual and audible information presented within the computer-simulated environment to sufficiently challenge the human subject 1050 by increasing visual and audible information rendered in the computer-simulated environment without detrimentally overloading the human subject 1050 with excessive visual and audible information.

An exemplary anxiety threshold function 1075 is provided in FIG. 1 which adjusts the sensory variables 1035 and the resultant complexity of the computer-simulated environment based on only pulse rate gathered from the digital sensors 1045 and passed through the sensing module 1040 to the control module 1001.

A normal pulse for a healthy adult spans 60 to 100 beats per minute. The pulse rate may vary and increase with anxiety. The exemplary anxiety threshold function in 1075 sets the upper anxiety value constant 1065 with an integer value of 100. This represents 100 beats per minute. The lower anxiety value constant 1070 is set at an integer value of 80. This represents 80 beats per minute. The value of 80 is set because 60-80 is still considered normal and executive functions may be successfully performed with additional stress-induced anxiety up to at least 80. If only a single threshold value was set, then the apparatus would "overrespond" to a movement above and below that single value.

Figure 2:
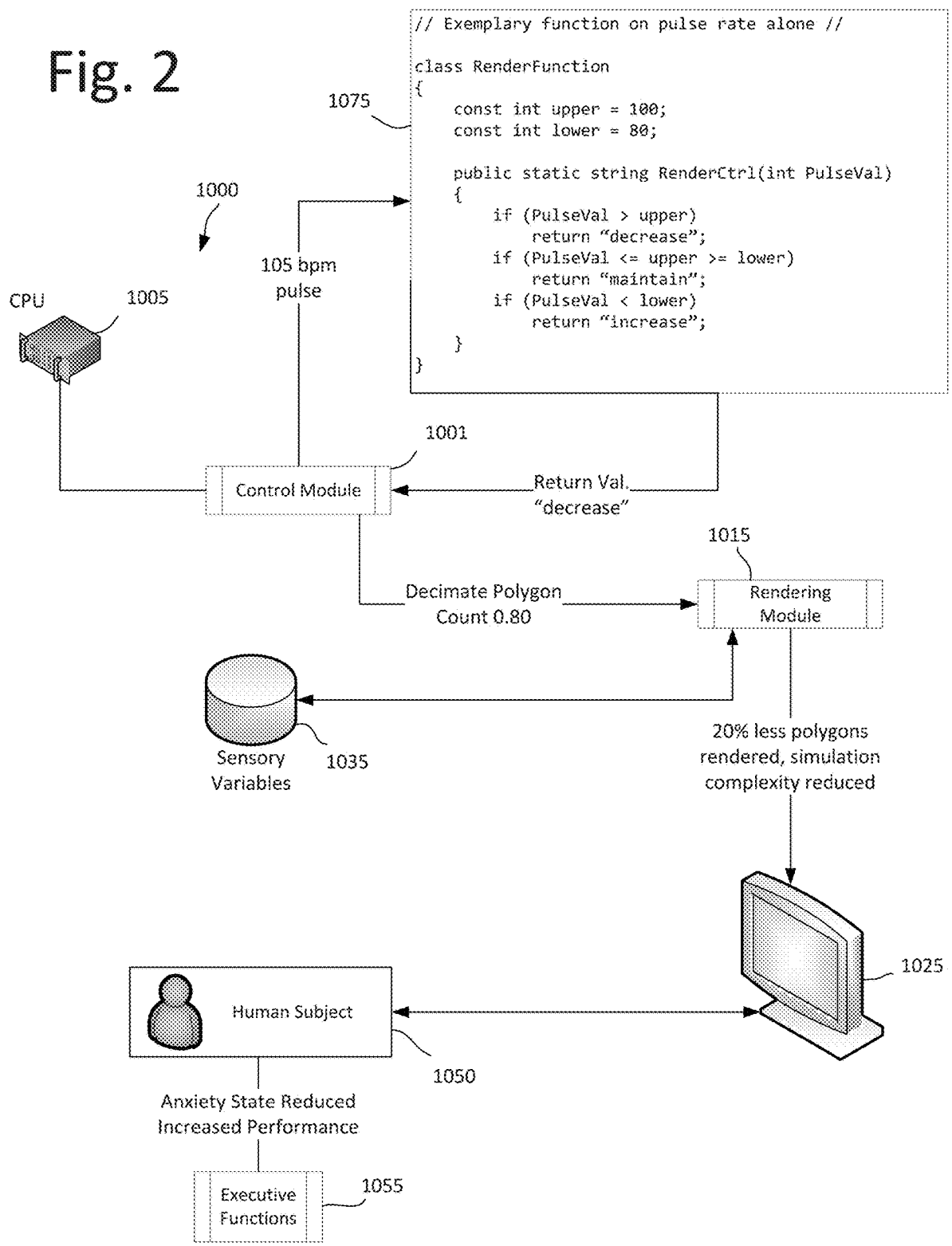
FIG. 2 is a diagrammatic view of an embodiment of the invention wherein a sensor-detected high pulse rate input value causes the computer processor to execute a function stored in computer memory to decrease polygon counts rendered to a display device thereby lowering subject anxiety.

In FIG. 2, a value of 105 beats per minute is received by the anxiety threshold function 1075. As the value of 105 exceeds the upper-value threshold 1065, the function 1075 returns a value of "decrease" to the control module 1001. This instructs the control module (in this example) to decimate (reduce) the polygon count of the rendered computer environment by 20%. The rendering module 1015 then renders 20% less polygons and the simulation complexity is thereby reduced. The intended effect on the human subject 1050 is to reduce anxiety state and increase the performance of the tasked executive functions 1055. This allows the therapeutic session to continue without "breaking" the human subject by overstimulation resulting in detrimental anxiety levels.

Figure 3:
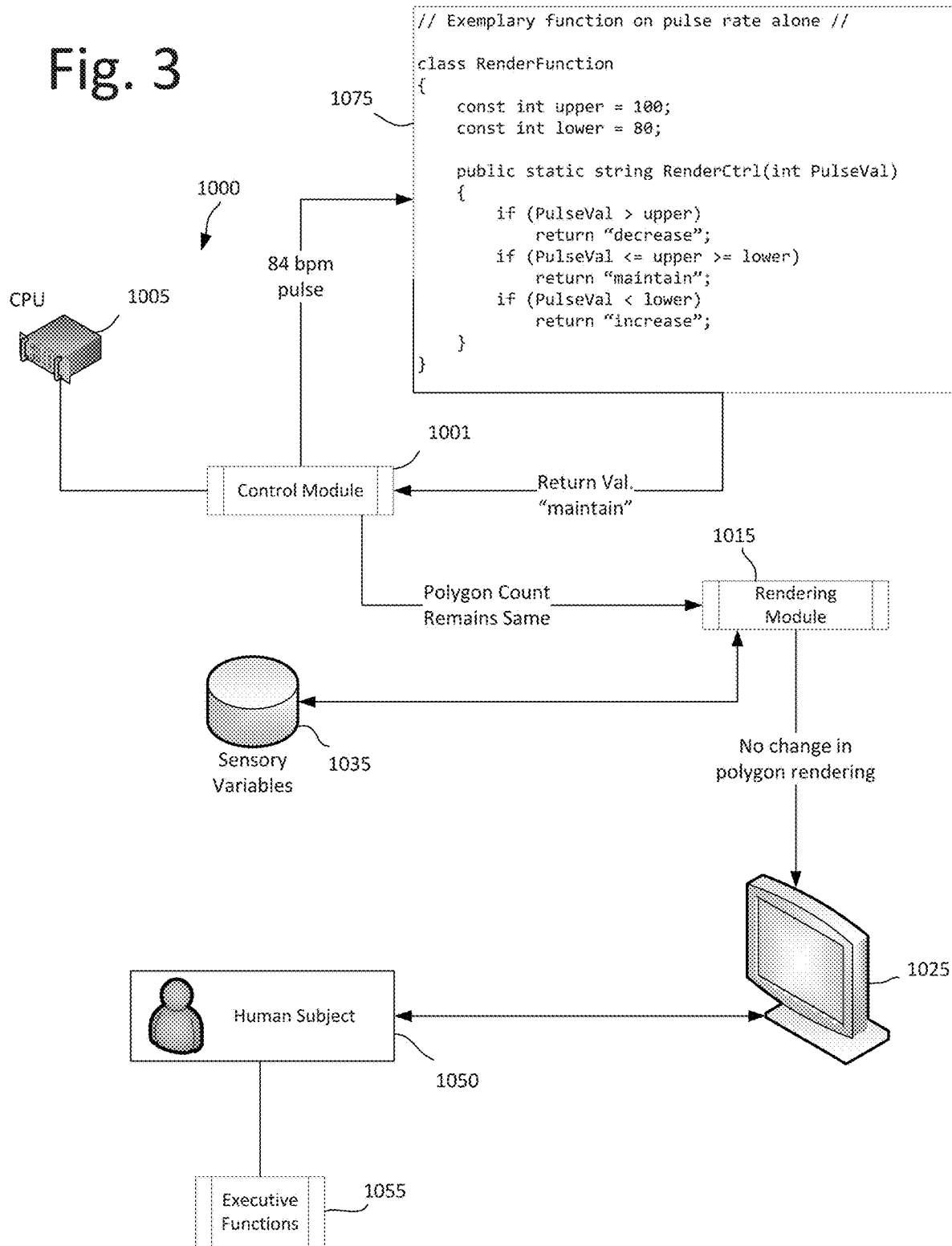
FIG. 3 is a diagrammatic view of an embodiment of the invention wherein a sensor-detected pulse rate input value is within thresholds causing the computer processor to maintain the current level of simulation complexity (with regard to polygon count).

In FIG. 3, a value of 85 beats per minute is received by the anxiety threshold function 1075. As the value of 85 is between the upper-value threshold 1065 of 100 and the lower value threshold 1070 of 80, the function 1075 returns a value of "maintain" to the control module 1001. This instructs the control module (in this example) to maintain the same polygon count of the rendered computer environment. The rendering module 1015 renders the same number of polygons and the simulation complexity is thereby kept constant. The intended effect on the human subject 1050 is to produce no change in the anxiety state and thereby extend the therapeutic session to continue to develop proficiency in the tasked executive functions 1055.

Figure 4:
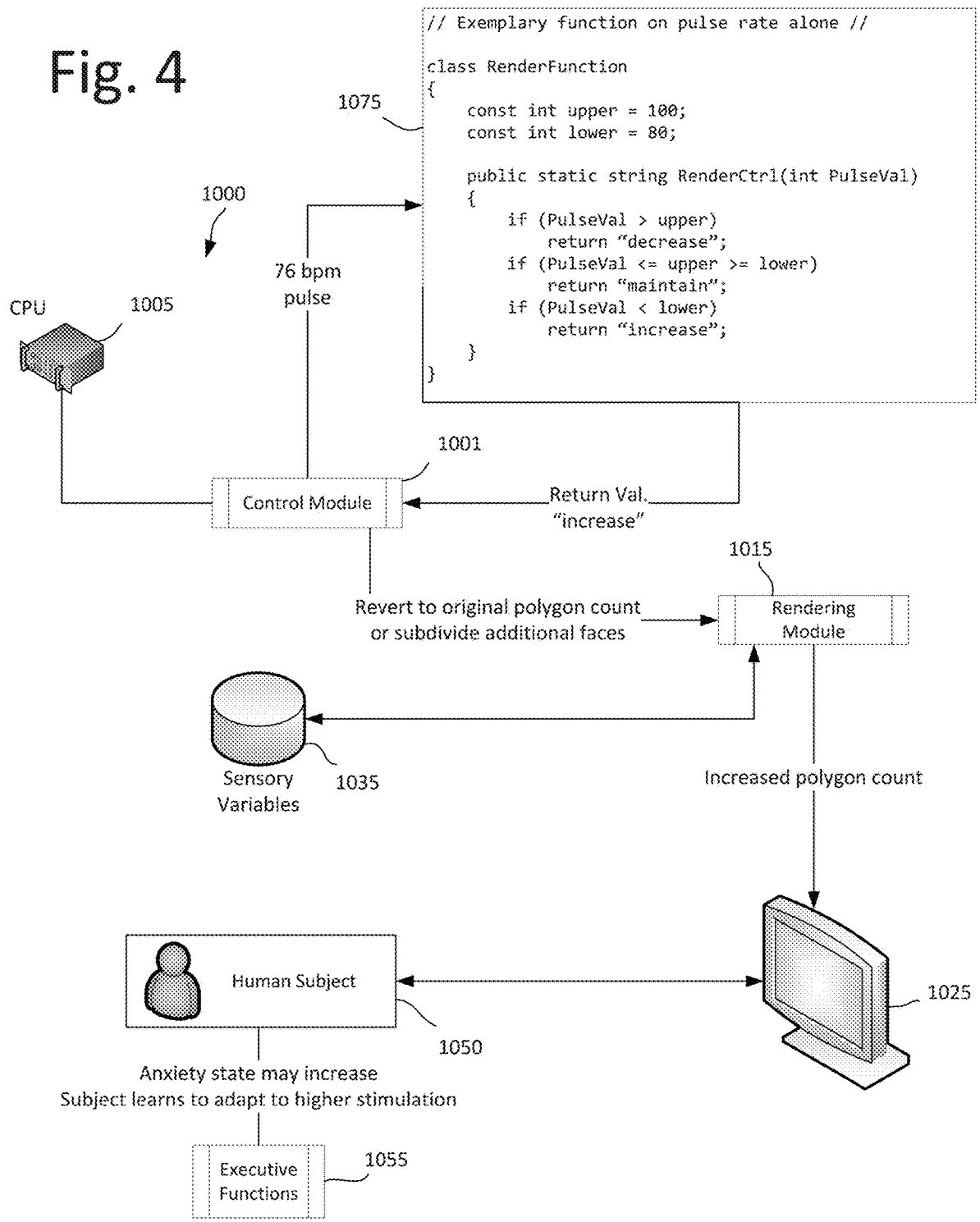
FIG. 4 is a diagrammatic view of an embodiment of the invention wherein a sensor-detected pulse rate input value is within below thresholds causing the computer processor to increase the current level of simulation complexity by reintroducing or increasing polygon counts thereby potentially increased human subject anxiety in a controlled manner.

In FIG. 4, the human subject 1050 is not sufficiently challenged by the executive task and/or the computer-simulated environment A value of 76 beats per minute is received by the anxiety threshold function 1075. As the value of 76 is below the lower value threshold 1070 of 80, the function 1075 returns a value of "increase" tithe control module 1001. This instructs the control module (in this example) to increase the polygon count of the rendered computer environment (or revert to the original polygon count). The rendering module 1015 renders an increased number of polygons and the simulation complexity is thereby increased. The intended effect on the human subject 1050 is to produce a more challenging environment even at the possible cost of slowly increasing anxiety state. This maintains the therapeutic session efficacy in the tasked executive functions 1055 and mitigates the human subject 1050 suffering from complacency or boredom.

Figure 5:
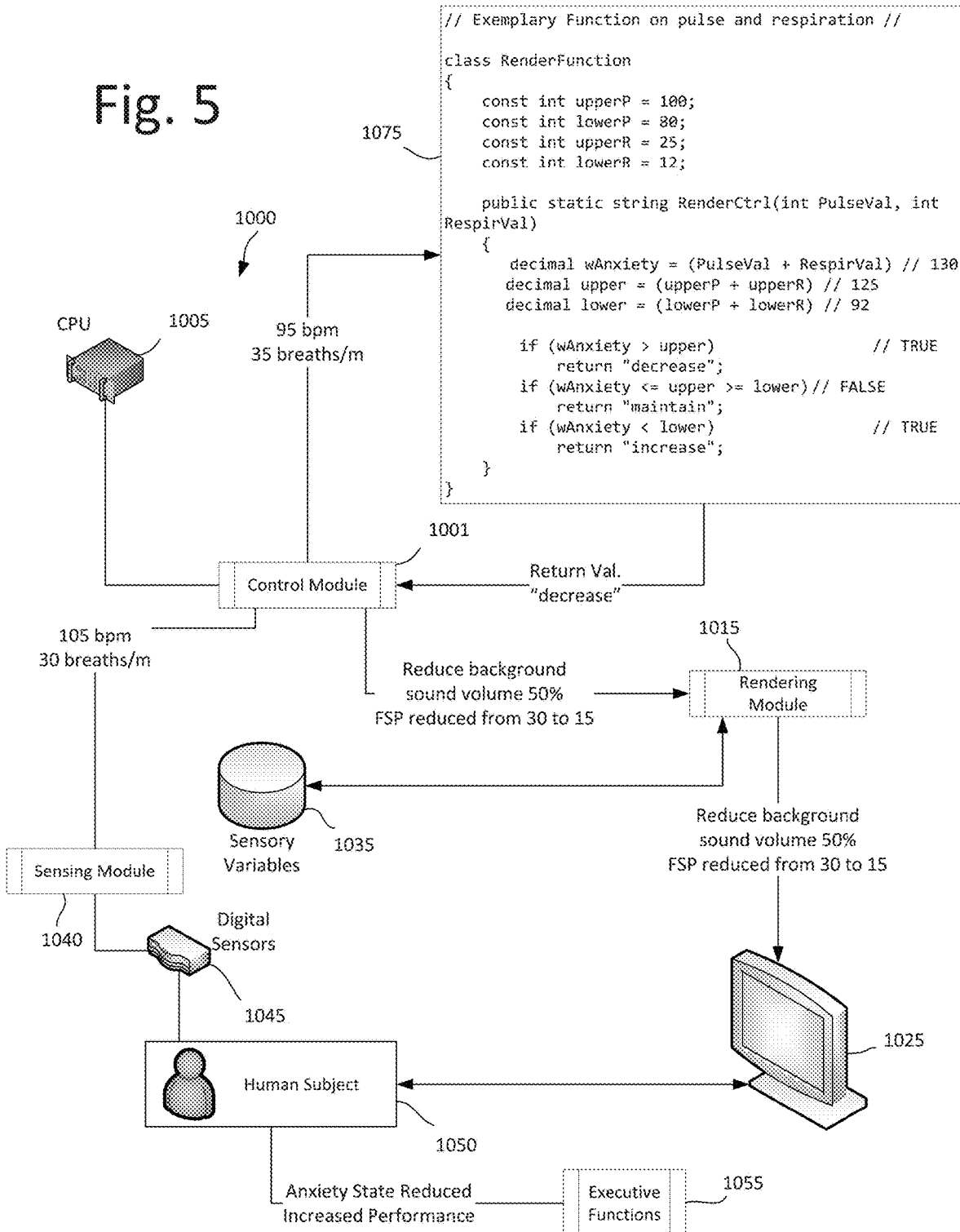
FIG. 5 is a diagrammatic view of an embodiment of the invention wherein multiple sensor values (pulse and respiration) are inputted into the processor-executed function to return a directive to reduce simulation complexity, namely lowering background sound and frames-per-second rendered.

FIG. 5 shows an alternative embodiment of the anxiety threshold function 1075 using two physiological values (pulse and respiration) and also modifying two separate aspects of the computer-simulated environment. In this embodiment, human subject 1050 has a detected pulse of 95 and a respiration rate of 35 breaths per minute. Anxiety threshold function 1075 receives both values. The normal respiration rate for an adult at rest is 12 to 20 breaths per minute. A respiration rate under 12 or over 25 breaths per minute while resting is considered abnormal. The human subject's pulse (at 95) is below the upper constant integer value of 100 but below the lower constant integer value of 80. The human subject's respiration of 35 breaths per minute is likewise well above normal and an indicium of anxiety. The function applied in FIG. 5 is unweighted combining the values linearly, but it would be known to a person of ordinary skill in the art to weigh the physiological import of respiration versus pulse (or other measured factors as enumerated above). In this example, a value of "decrease" is returned to the control module 1001, which reduces background sound volume of the computer simulation by 50 percent and also reduces the rendered frames per second from 30 to 15. The intended therapeutic effect on the human subject 1050 is to reduce the anxiety level detected from abnormally high breathing rate which will increase his or her capability of successfully performing the executive functions 1055.

Figure 6:
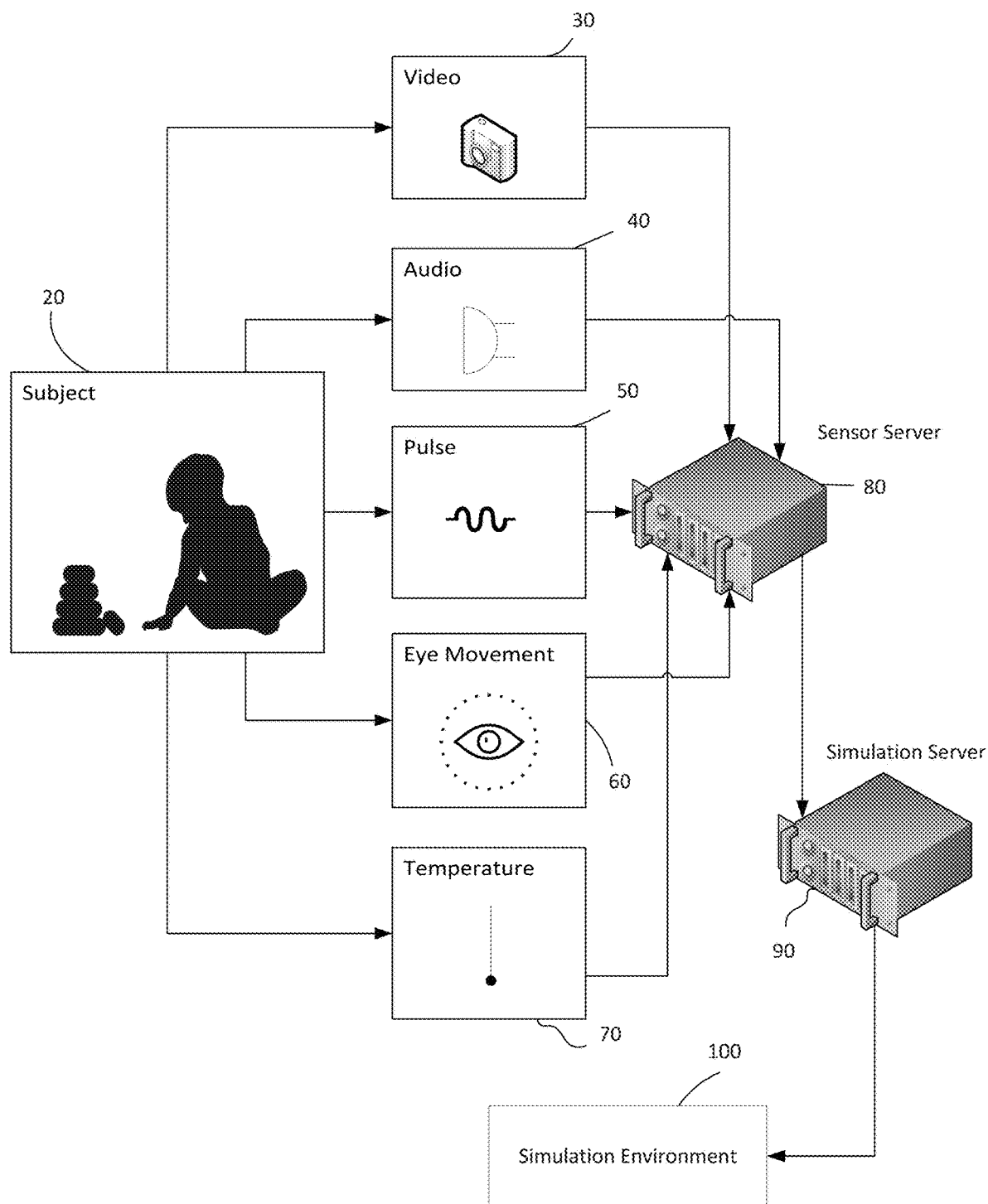
FIG. 6 is a diagrammatic view of sensor monitoring of a subject for anxiety.

Turning to FIG. 6, human subject 20 is engaged stacking rings on top of each other. A plurality of sensors monitors subject 20 including video 30, audio 40, pulse rate 50, eye movement 60 and temperature 70. Different sensor apparatuses may be applied based on the needs of the training, maturity of the subject and clinician preferences. For example, a wrist-based band may measure temperature, pulse and body movements. A microphone may be parabolic or lapel. The video may superimpose thermal (infrared) images to show body temperature changes.

Sensor data from sensors 30, 40, 50, 60 and 70 are sent to sensor server 80. The sensor data may be aggregated to form a total quantified anxiety level. The sensor data may be weighted to each detected characteristic. For example, a normal heart rate is 60 to 100 beats per minute but may increase measurably due to anxiety. A resting heart rate for the subject may be obtained prior to the computer simulation and increases or decreases from that starting rate may be weighted formulaically.

Sensor data related to body temperature may be associated with anxiety-based vasoconstriction, which may cause the body to heat up very quickly. However, this may also be followed up by sweating, a natural response to vasoconstriction which may cause body temperature drops. Accordingly, in some monitoring situations, body temperature data may be coupled with a perspiration sensor to detect changes of impedance wherein a cool-down from anxiety-induced temperature elevation from vasoconstriction is not incorrectly associated with a reduction in anxiety but from sweating.

Clinical observations suggest abnormal gaze perception to be an important indicator of anxiety disorders. In addition, vigilance in anxiety disorders may be conveyed by fixations on sources of stress. These behaviors and others related to them may be monitored by eye-tracking by camera sensors and weighted to anxiety levels. Speech patterns may be linked to both diagnosis and immediate anxiety levels based on activation, tonality, and monotony among other characteristics.

Sensor data from sensor server 80 is relayed to simulation server 90. The sensor data may be aggregated into one, total numeric value, or may be segmented into different subsets values for more granular control of the computer-simulated environment features.

Figure 7:
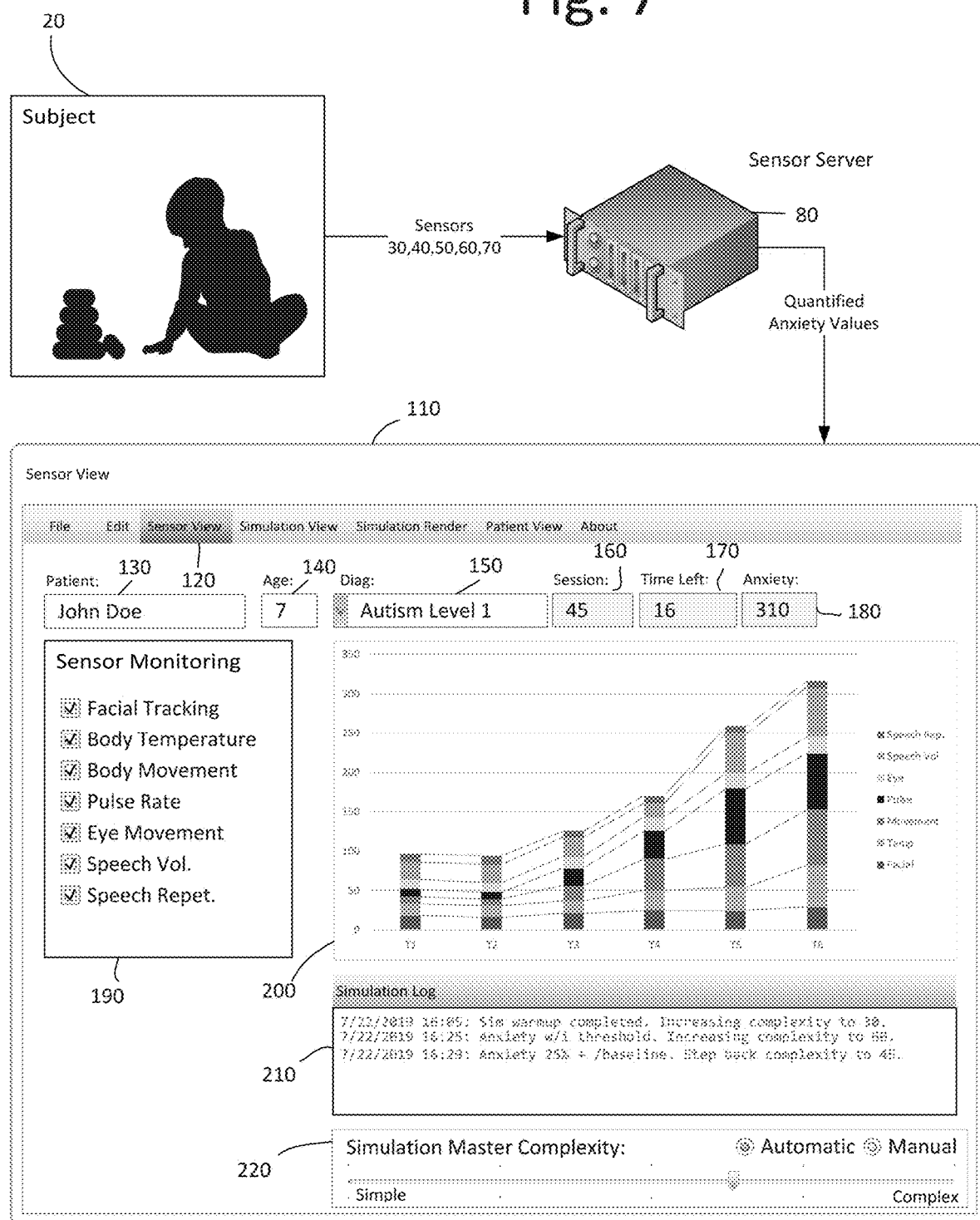
FIG. 7 is a graphics user interface view of sensor monitoring of a subject over time according to an embodiment of the invention.

FIG. 7 shows a graphic user interface 110 of a sensor view for patent 130. Various controls on the interface include patient age 140, diagnosis 150, total session time 160, time left in the current session 170, and current anxiety level 180. An end user operating the interface may select from an array 190 of sensors to individually select which types of data to receive. Anxiety aggregate graph 200 shows a relatively steady increase in subject 20 anxiety levels from six points in time (T1-T6). Simulation log 210 reports on incoming sensor data and adjustments automatically made in the computer simulation. Dialog control 220 is a master complexity slider for the computer simulation set to automatic mode. The slider in dialog control 220 automatically moves left as the system reduces complexity responsive to elevated subject anxiety and moves right as the subject's anxiety level decreases. Selecting the manual radio button in dialog control 220 permits the end user to override the overall complexity of the computer-simulated environment but the computer nevertheless intelligently and automatically reduces or increases multiple features of simulation complexity for the end user.

Figure 8:
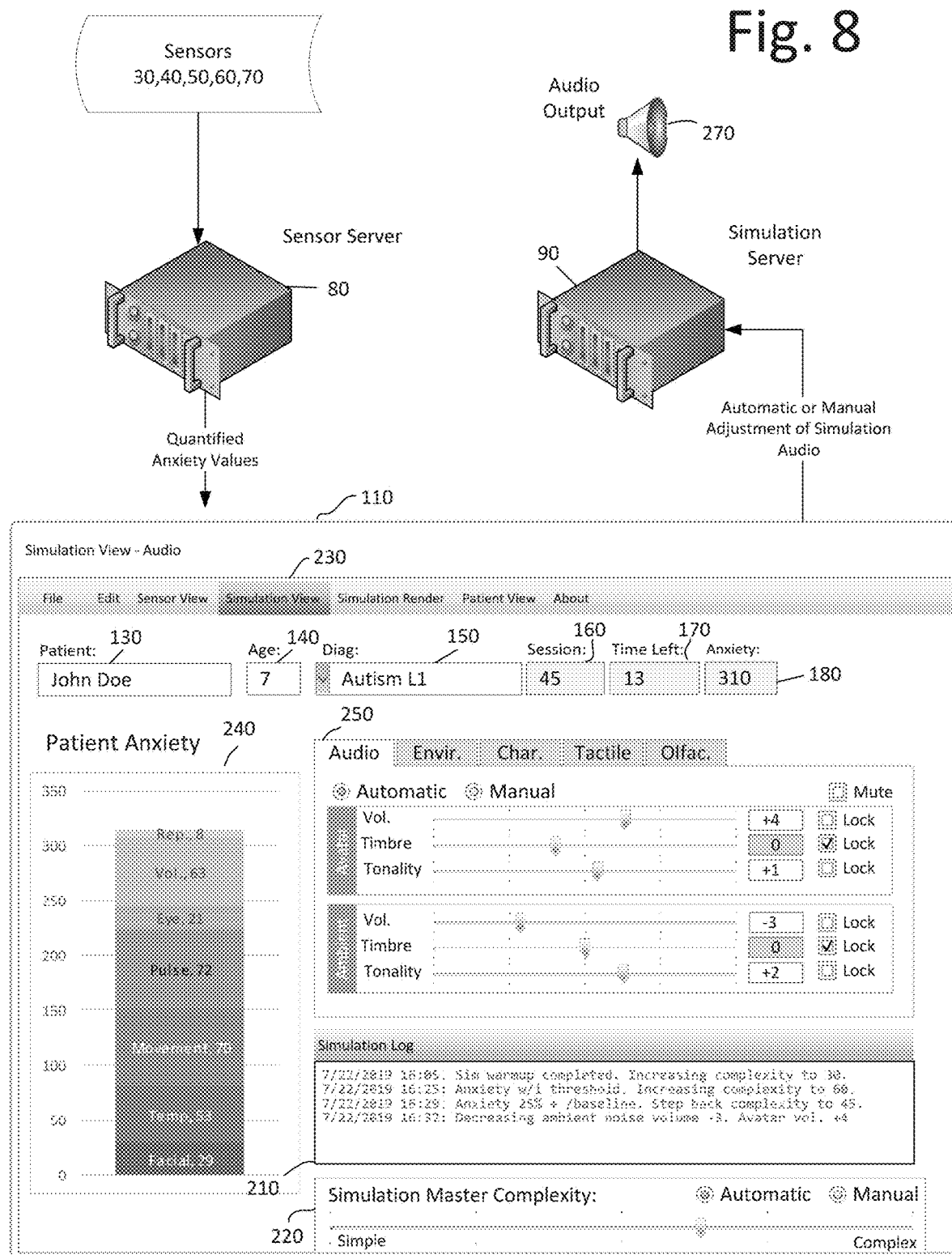
FIG. 8 is a graphics user interface view of an audio control dialog for the simulation output according to an embodiment of the invention.

In FIG. 8, simulation view 230 is shown wherein audio control tab 250 is activated. Radio button "Automatic" is selected in control tab 250 so both ambient noises and avatar audio are automatically controlled by the computer. However, in this case, end user has manually "locked" or overrode the automated control for the timbre of the avatar and the timbre of the ambient noise in the simulation. Patient anxiety values for multiple sensors are presented as a stacked graph 240 in the interface view 230. Simulation log 210 shows that the computer, responsive to sensor-detected anxiety levels, decreased ambient noise volume but increased avatar speech volume.

Figure 9:
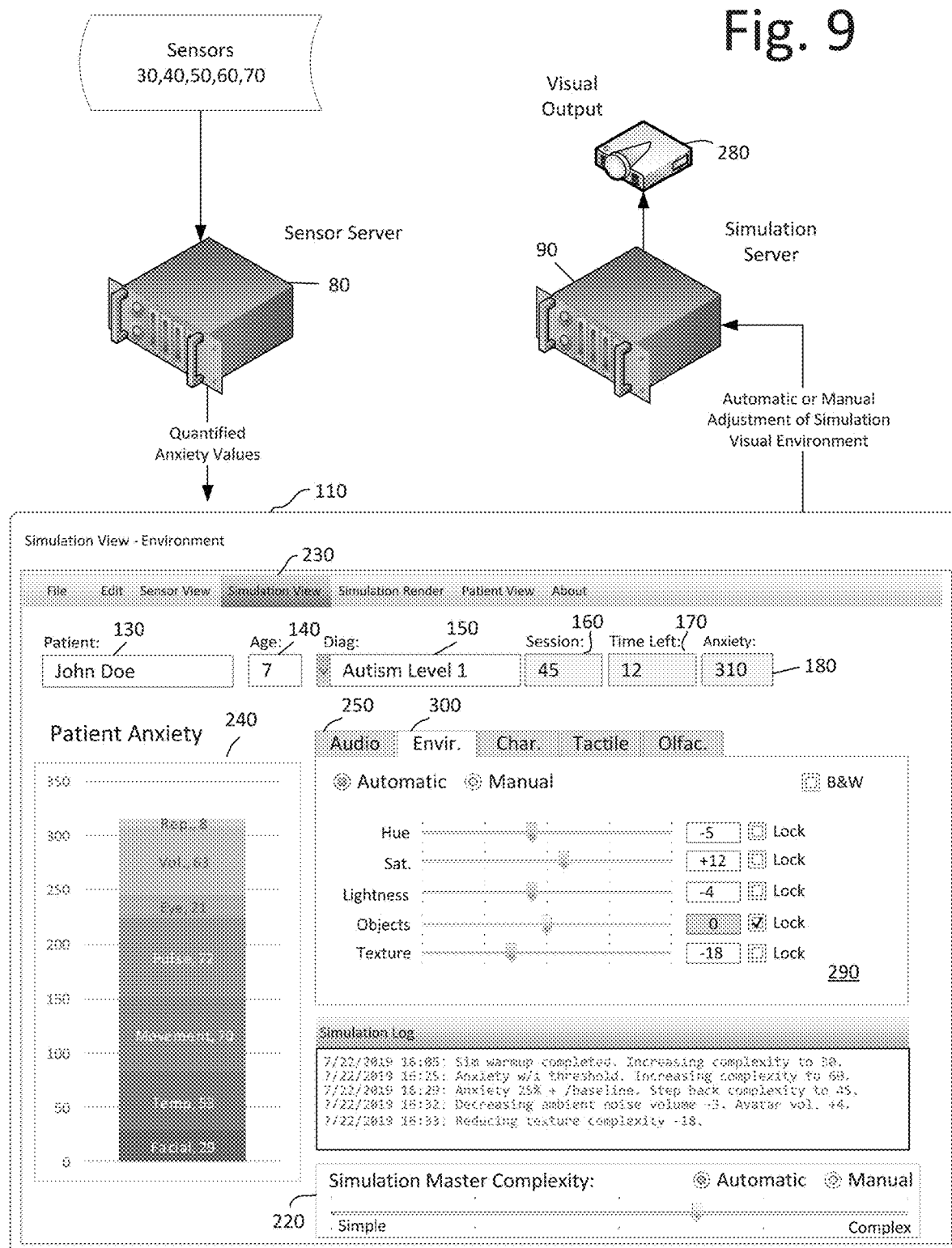
FIG. 9 is a graphics user interface view of an environmental control dialog for the simulation according to an embodiment of the invention.

In FIG. 9, simulation environment tab 300 is active and shows simulation features such as hue, saturation, lightness, number of objects and texture complexity. In this example, the number of objects is locked at zero (0) which, in this embodiment, means that the default number of objects is retained (none added, and none removed). Texture in the simulation has automatically been reduced. For some disorders, particularly those involving the processing of information, reducing texture complexity of objects and backgrounds in a simulation may reduce stress. For example, instead of a detailed, brick wall, the simulation may show a plain painted surface. In some embodiments of the invention, objects may have movement loops such as fish in a fish tank or a plant moving gently from a breeze. The movement of the object may be paused, slowed or speed up responsive to the sensed anxiety level of the subject. For example, an object may even be a monitor in the background of the simulated environment showing a newscast Such movement and content may cause anxiety which is detected by the sensors, so the content of the monitor is changed to landscape images or the monitor is virtually "turned off" to a black screen.

Figure 10:
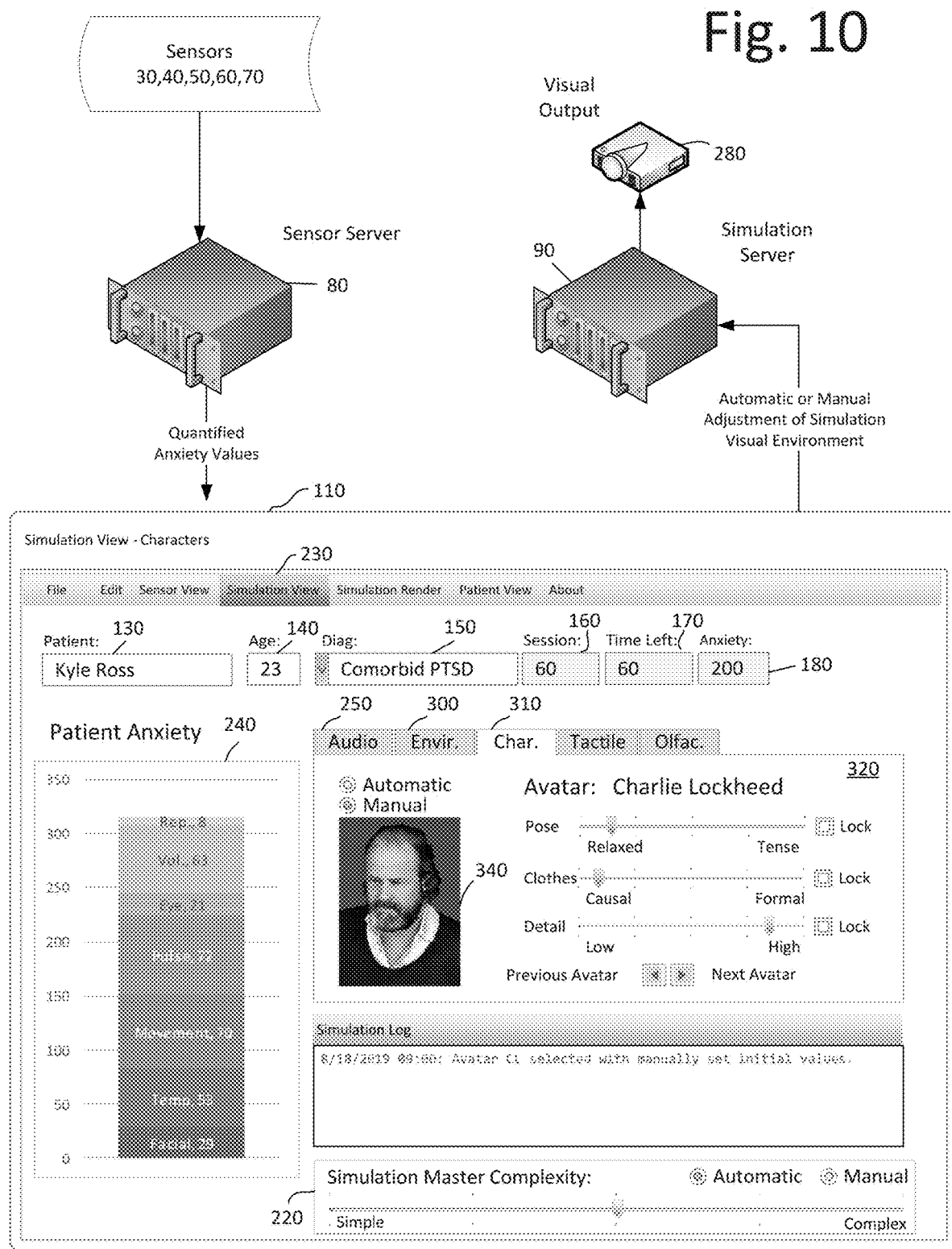
FIG. 10 is a graphics user interface view of a character control dialog for the simulation according to an embodiment of the invention showing a first avatar.
Figure 11:
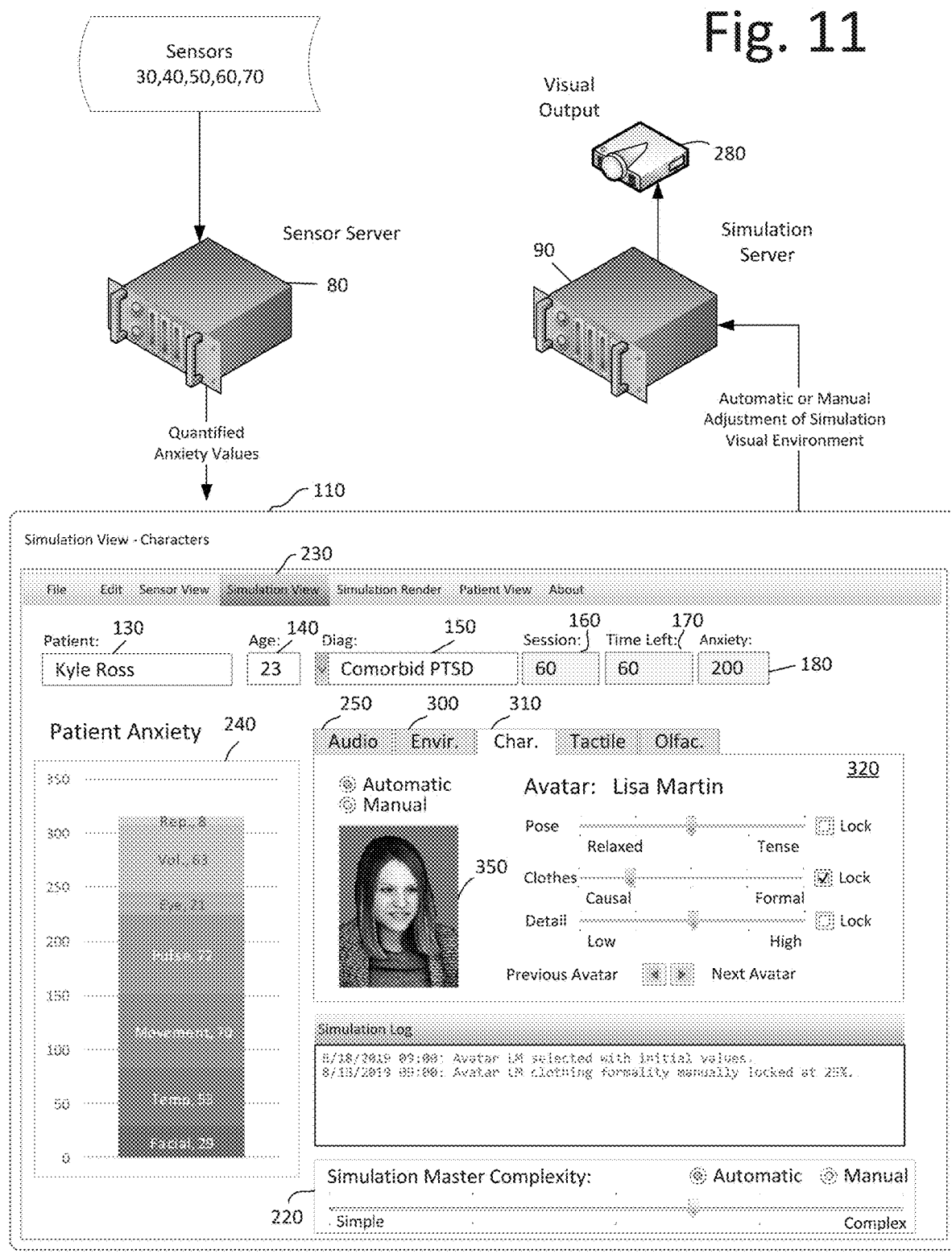
FIG. 11 is a graphics user interface view of a character control dialog for the simulation according to an embodiment of the invention showing a second avatar.

In FIG. 10, a different subject is entered into the interface diagnosed with PTSD. Tab 310 shows a first avatar character. Settings for the first avatar have a number of features including pose states, clothing options, polygon detail (e.g., realism). FIG. 11 shows a second avatar for the same simulation and subject.

Figure 12:
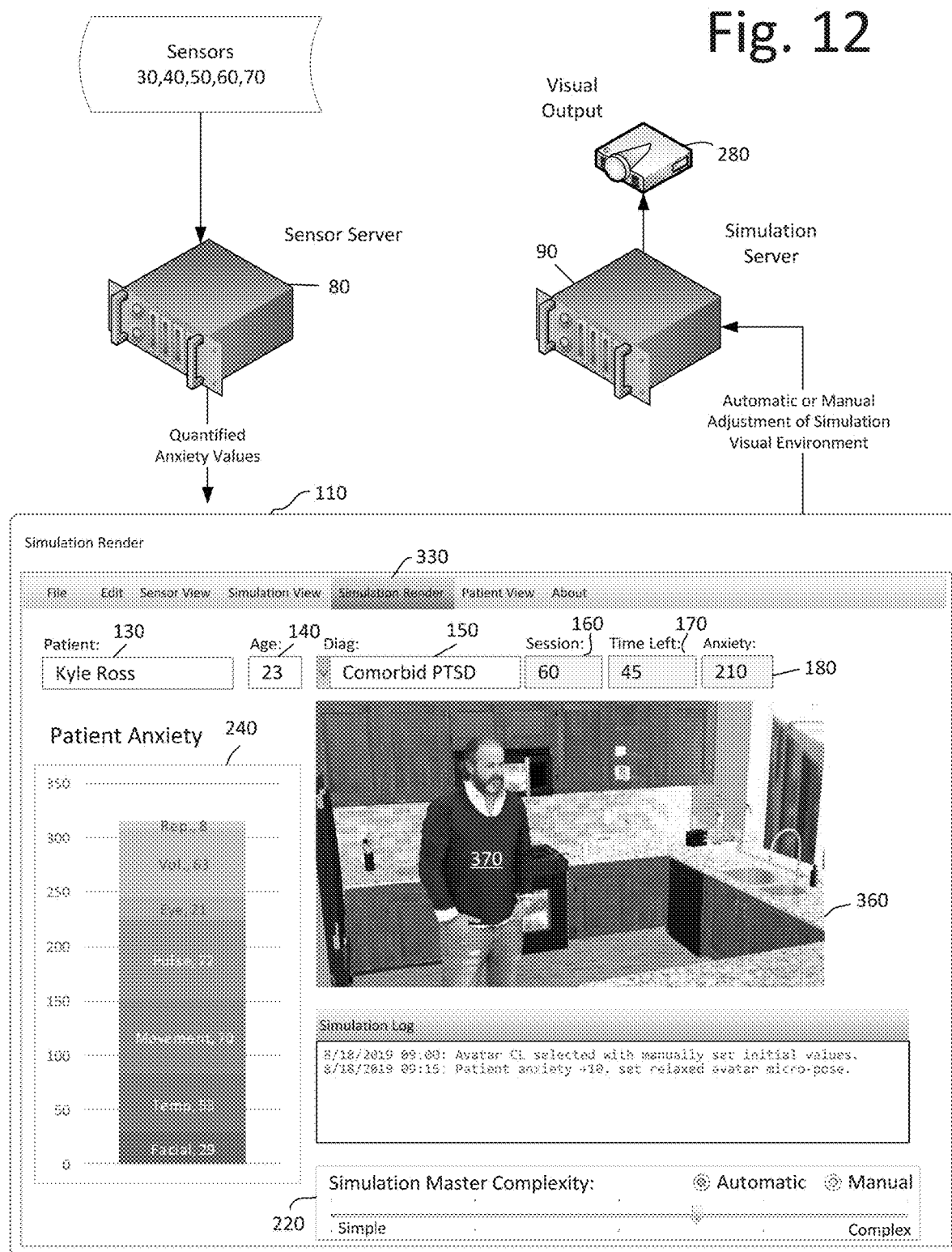
FIG. 12 is a graphics user interface view of a simulation rendering of an avatar in a kitchen environment according to an embodiment of the invention.
Figure 13:
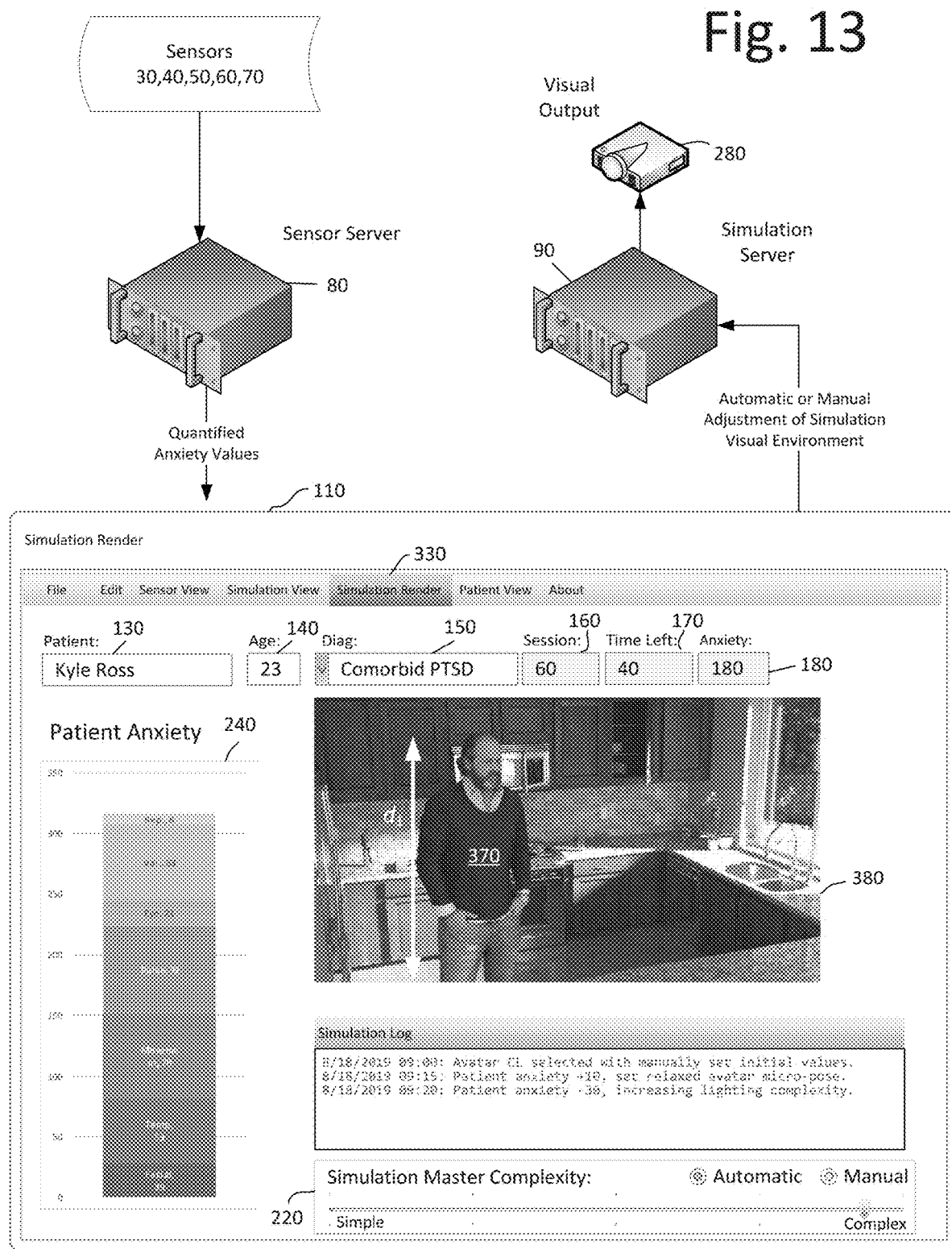
FIG. 13 is a graphics user interface view of a simulation rendering of an avatar in a kitchen environment with more complex lighting and texturing according to an embodiment of the invention.
Figure 14:
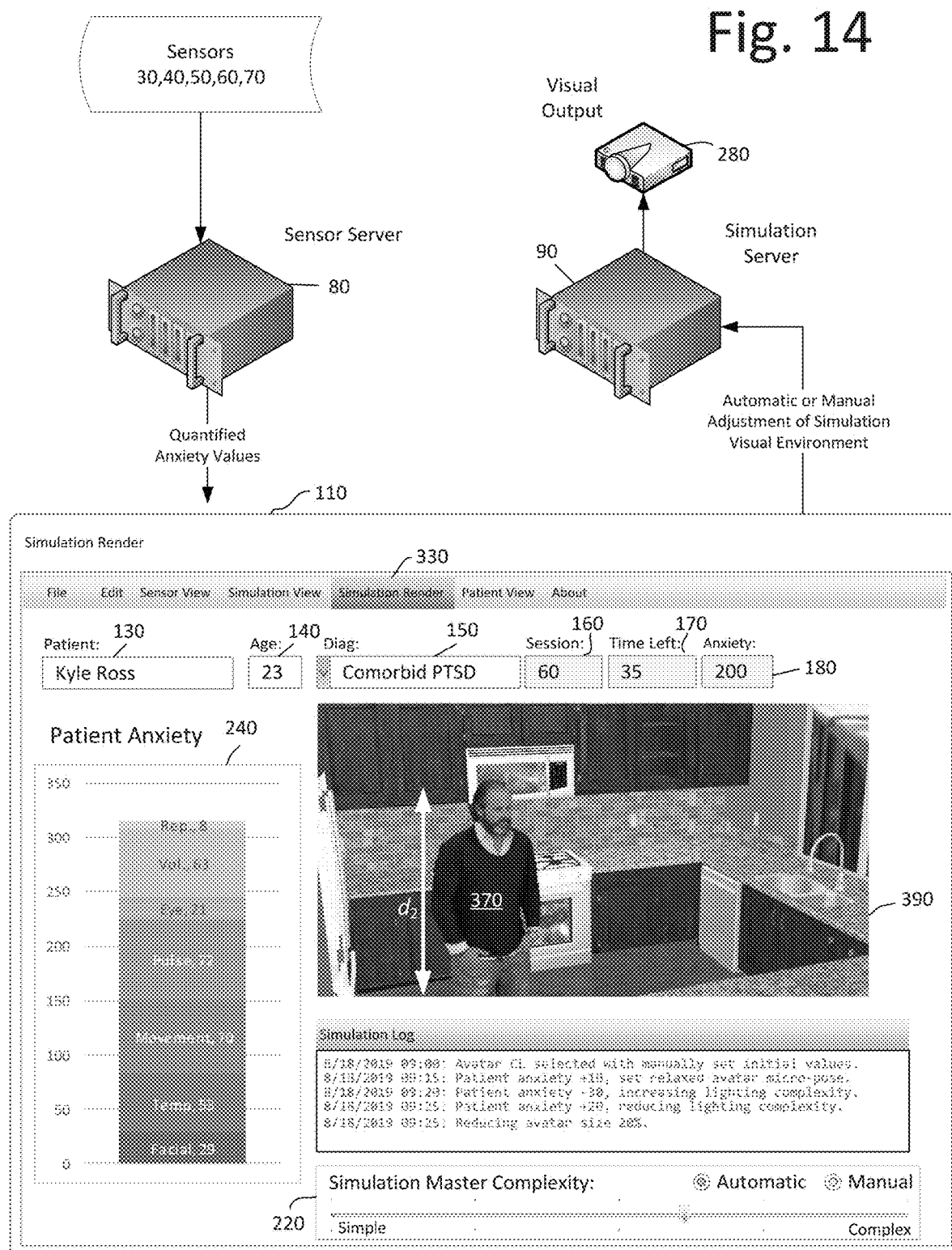
FIG. 14 is a graphics user interface view of a simulation rendering of a reduced-sized avatar in a kitchen environment according to an embodiment of the invention.

In FIG. 12, a simulation render dialog 330 is shown with a 2D simulation image 360 of first avatar 370 in a kitchen environment. In FIG. 13, the sensor detects that the subject 20 has reduced anxiety levels so the complexity of the simulation lighting is increased to add more realism. FIG. 13 also shows a distance d1 associated with the height of first avatar 370 in the virtual environment. However, in FIG. 14, sensor data conveyed an increase in subject 20 anxiety, so lighting complexity is reduced and optionally, the height of first avatar 370 is reduced 20% to d2.

Figure 15:
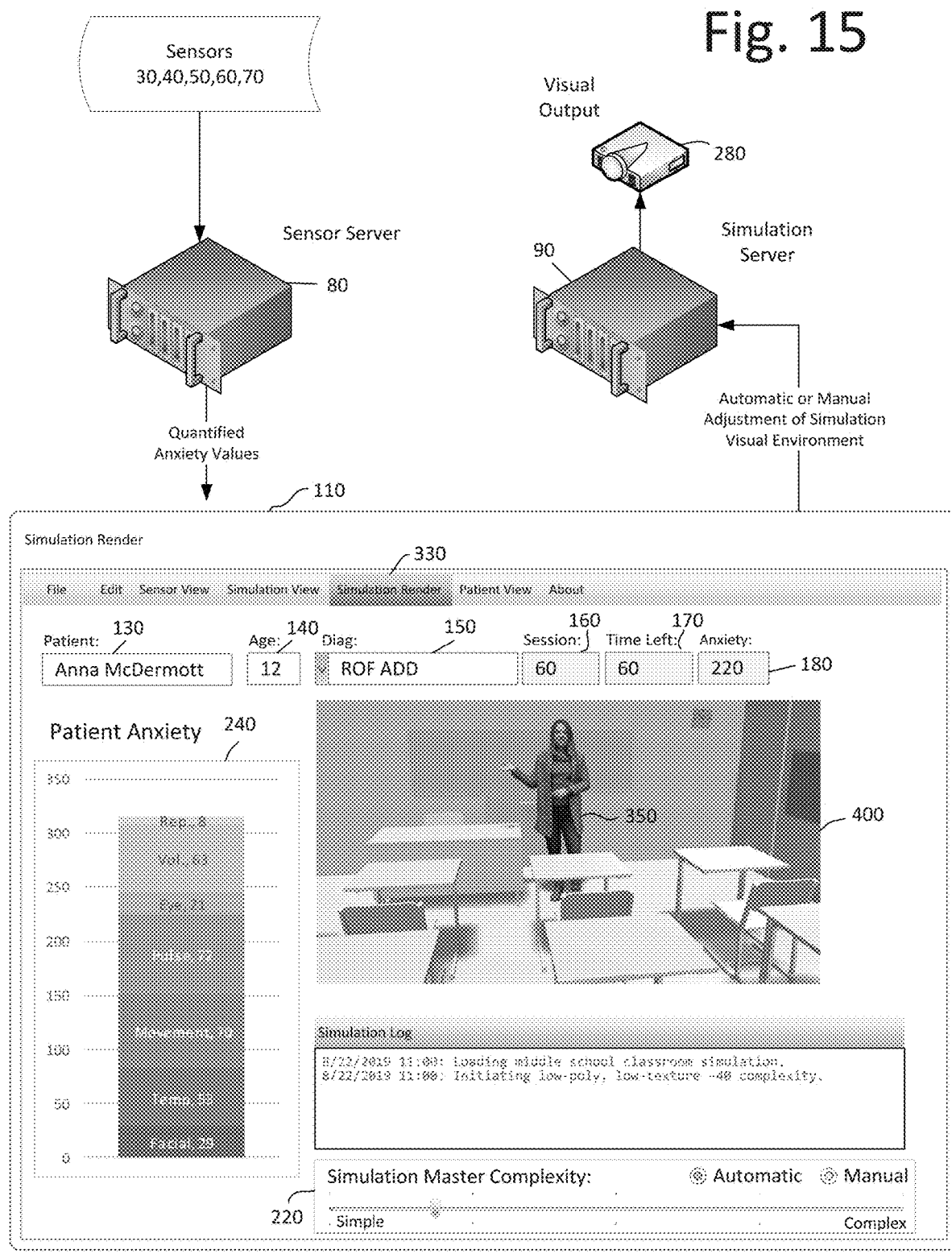
FIG. 15 is a graphics user interface view of a photo-realistic avatar in a classroom environment according to an embodiment of the invention.
Figure 16:
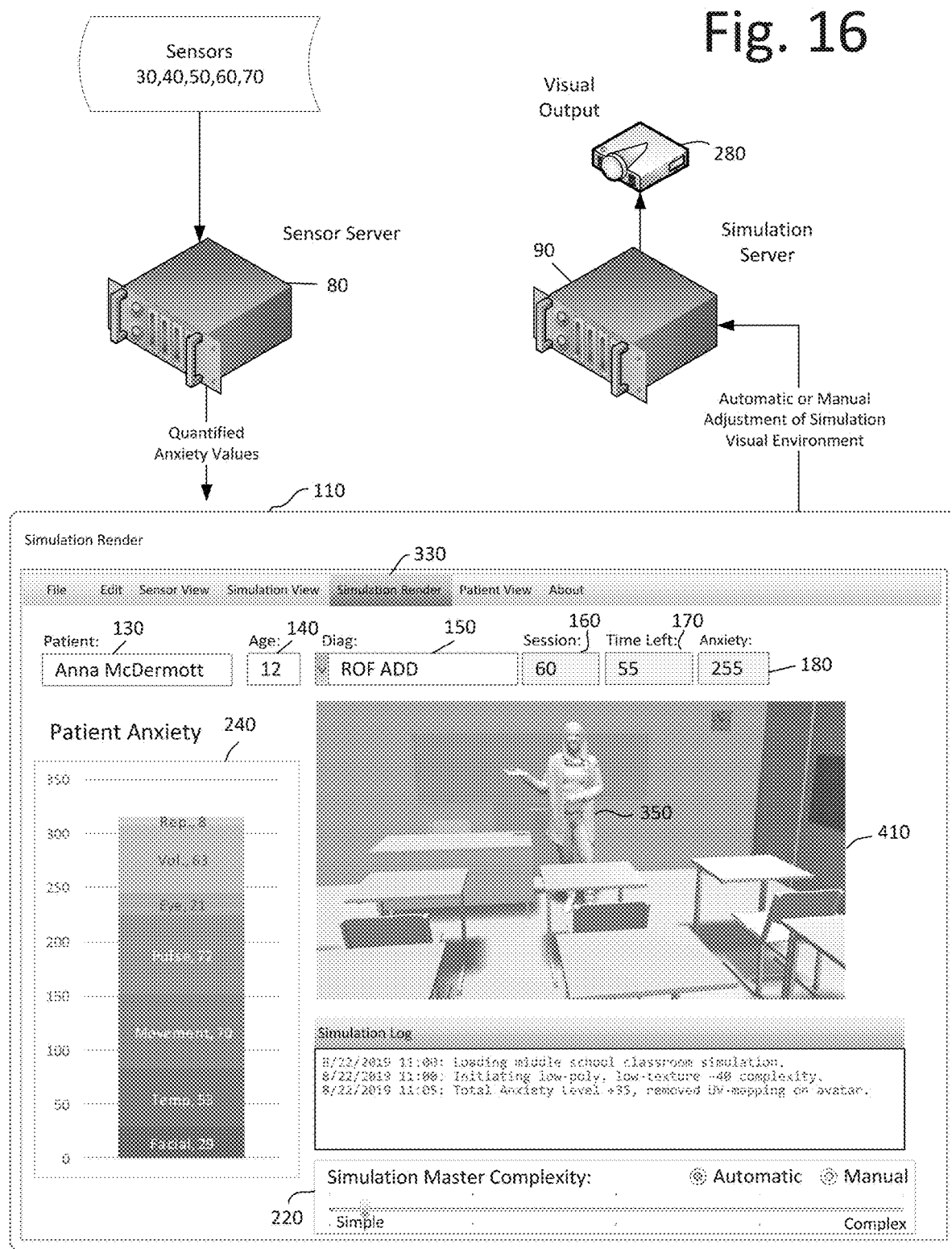
FIG. 16 is a graphics user interface view of a simplified avatar without UV mapping in a classroom environment according to an embodiment of the invention.

FIG. 15 shows an interface for a 12-year old patient diagnosed with Ring of Fire Attention Deficient Disorder in a middle school classroom environment. The simulation environment that subject 20 observes is shown in window 400 with second avatar 350. Simulation log notes that the schoolroom environment was intentionally initiated with a low-texture level and low polygon count to reduce initial stress on this particular subject Second avatar 350 is rendered photorealistic. FIG. 16 indicates an increase in anxiety for subject 20 so second avatar 350 is simplified by removing the photorealistic UV mapping. Second avatar 350 is conveyed in a revised simulation window 410 with less complexity which is indicated further by the far-left position of the slider in dialog control 220.

Figure 17:
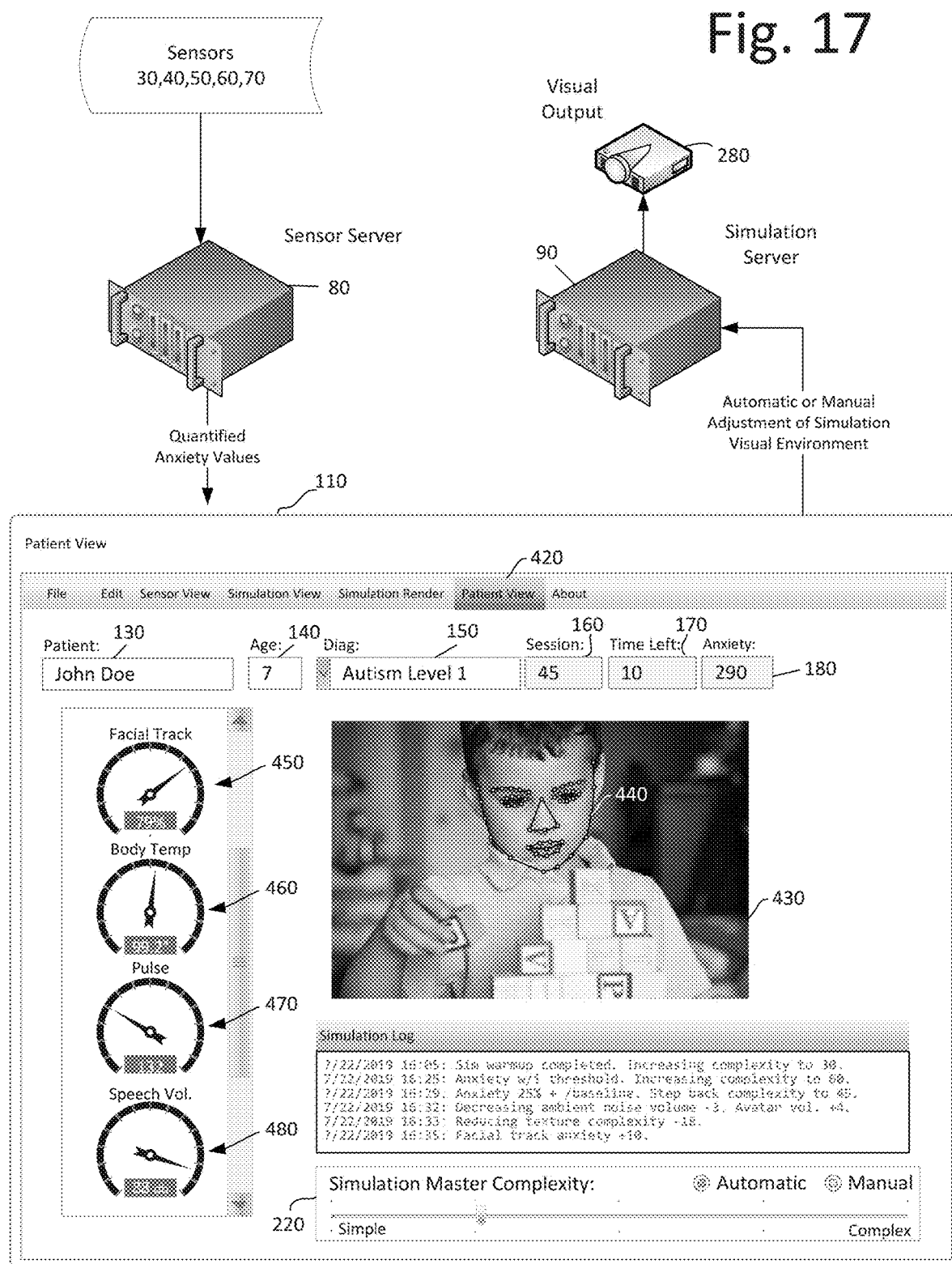
FIG. 17 is a graphics user interface view of a camera view of a human subject with facial tracking points superimposed according to an embodiment of the invention.

FIG. 17 returns to the 7-year old subject diagnosed with Autism Level 1 as previously shown in FIGS. 7-8. Patient view 420 is shown with a video feed 430 of the patient interacting with blocks. Facial tracking points 440 are overlaid on video feed 430, which is translated into an anxiety value 450 along with body temperature 460, pulse 470 and speech volume 480.

Figure 18:
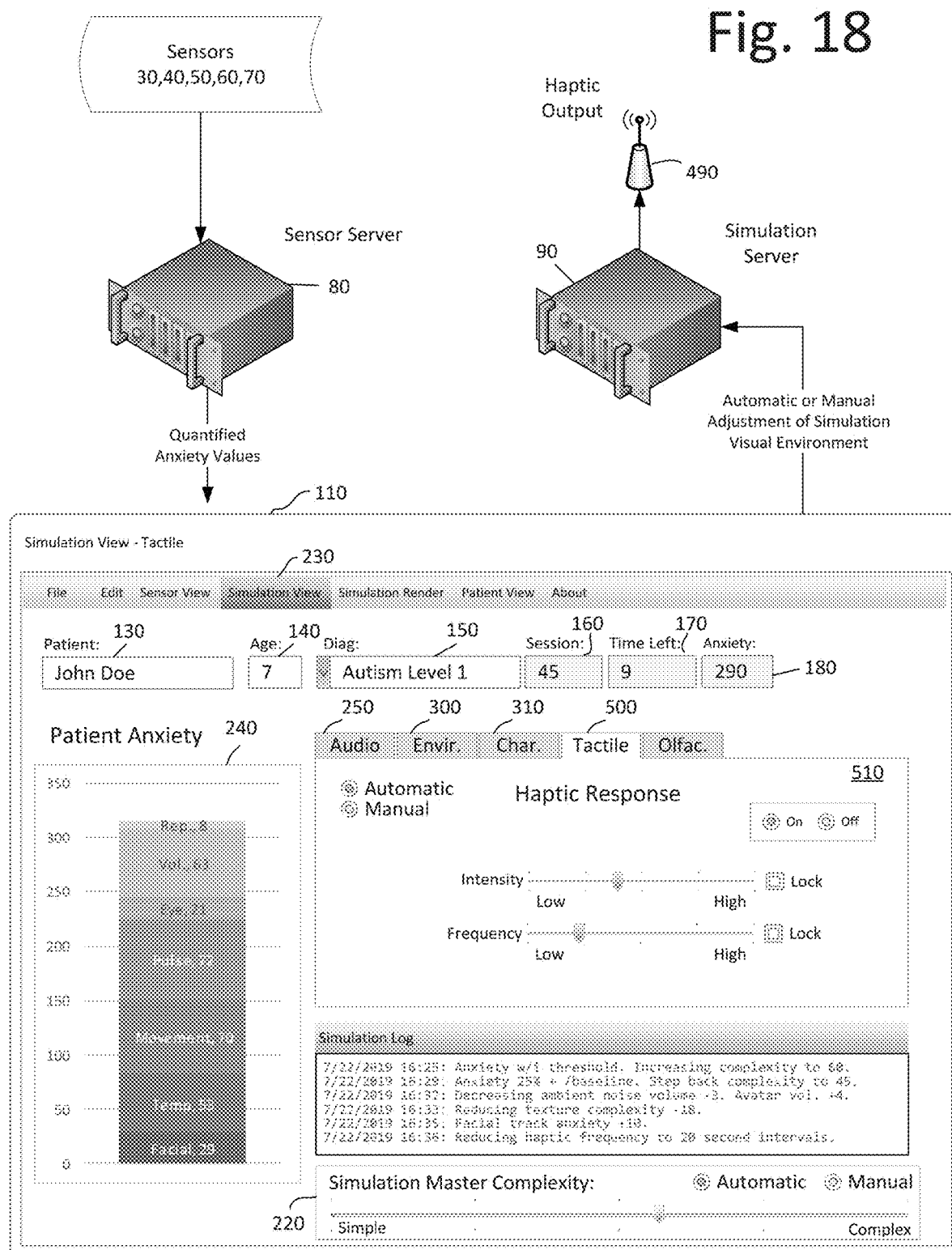
FIG. 18 is a graphics user interface view of a haptic (tactile) control dialog according to an embodiment of the invention.
Figure 19:
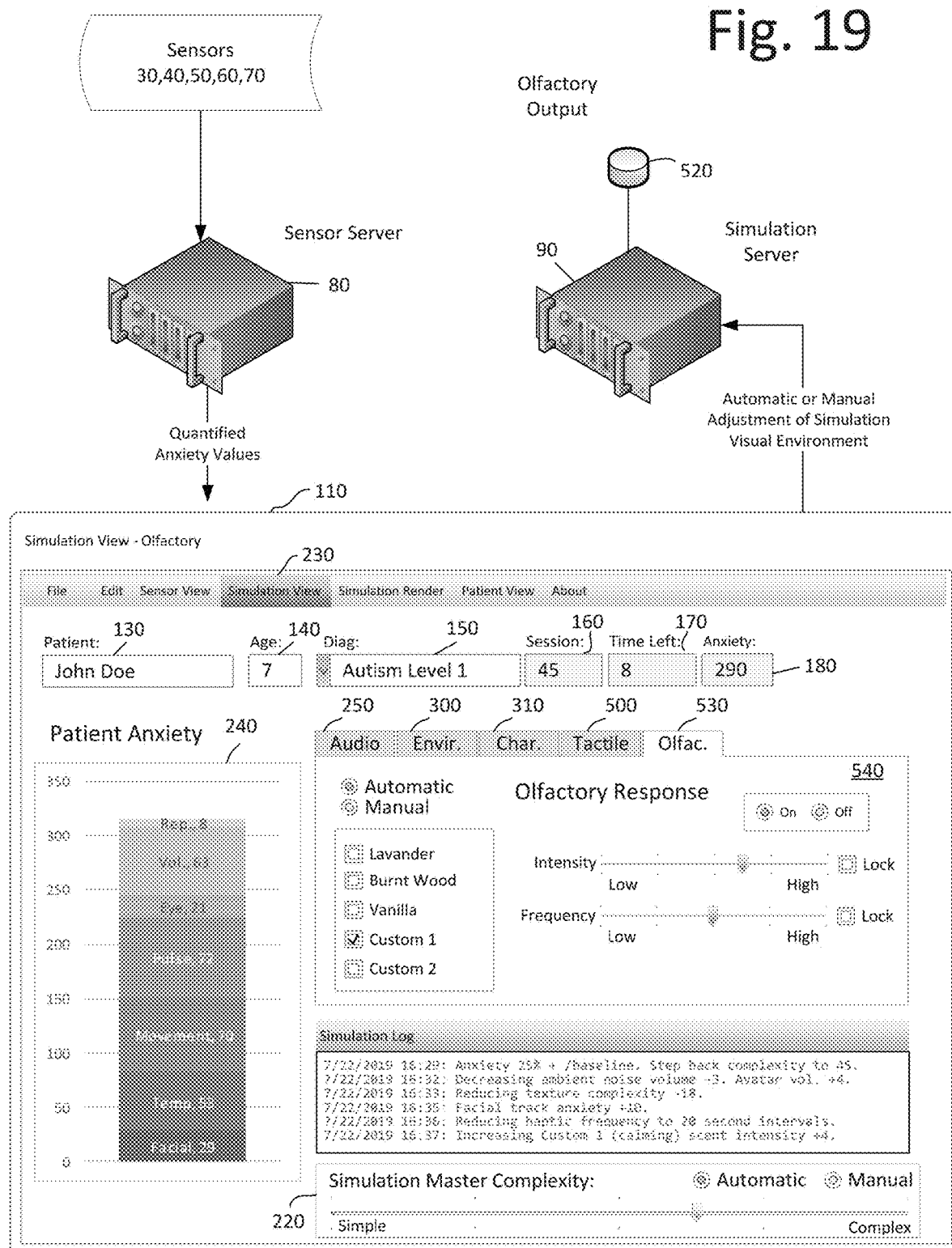
FIG. 19 is a graphics user interface view of an olfactory sense control dialog according to an embodiment of the invention.

FIG. 18 returns to simulation view 230 with tactile tab 500 active showing tactile dialog 510. The computer automatically controls haptic response settings for intensity and frequency. The haptic response may be a vibrational device affixed to the subject's limb, on a chair, under a play mat or within a toy being manipulated such as a stuffed animal. FIG. 19 shows olfactory tab 530 active displaying olfactory control dialog 540. It may control one or more scent diffusers that atomize mixtures of propylene glycol and scent elements.

Figure 20:
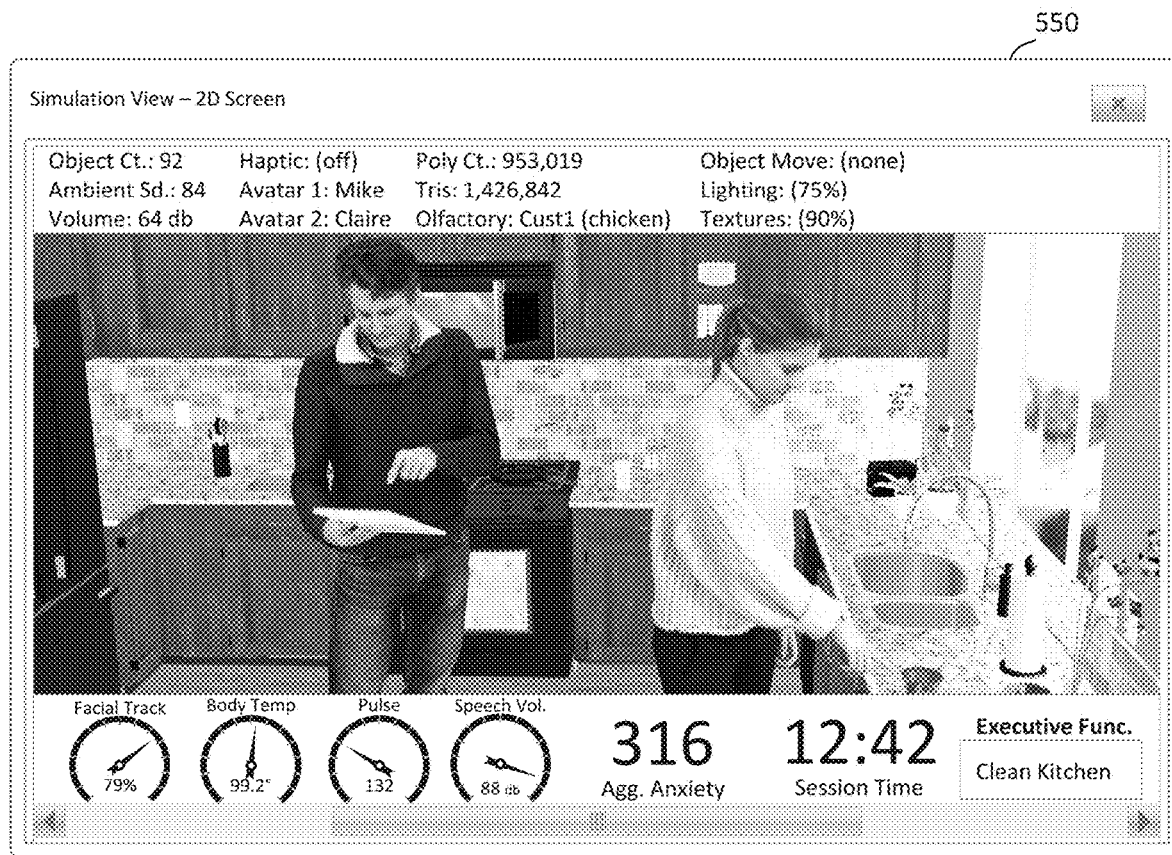
FIG. 20 is a graphics user interface view of a simulation view showing two avatars in a moderately complex kitchen environment according to an embodiment of the invention.
Figure 21:
FIG. 21 is a graphics user interface view of a simulation view showing two avatars in a reduced complexity kitchen environment according to an embodiment of the invention.

The computer-simulated environment is shown in a 2D presentation in FIGS. 20 and 21. In FIG. 20, a computer interface is provided that shows two avatars (Mike and Claire) in a kitchen setting. Data on the top of the interface show 92 objects in the scene. Ambient sound complexity (e.g., dishwasher, chirping birds, refrigerator compressor) is at level 84. The maximum sound volume is 64 dB. The polygon count of the simulation is 953,019, and the triangle count is 1.4 million. None of the non-avatar objects are moving. Lighting complexity is 75% and textures on surfaces are 90% complexity. The aggregate anxiety level of the subject is 316 at 12 minutes and 42 seconds into a session to develop executive functions in the context of cleaning a kitchen. A scent diffuser is atomizing a solution conveying the smell of cooked chicken to the subject.

In FIG. 21, the computer makes modifications to the computer-simulation environment of FIG. 20 to reduce complexity and thus lower anxiety levels. Twenty-four objects are removed from the countertop including plants, a paper towel roll, a toaster, a cutting board, a cup of spoons, and various other objects. Ambient sounds are reduced, and the maximum sound is at 45 decibels. The polygon and triangle counts are reduced, and the scent diffuser turned off. Lighting complexity is reduced and textures such as those on the cabinets and counters are removed.

Figure 22:
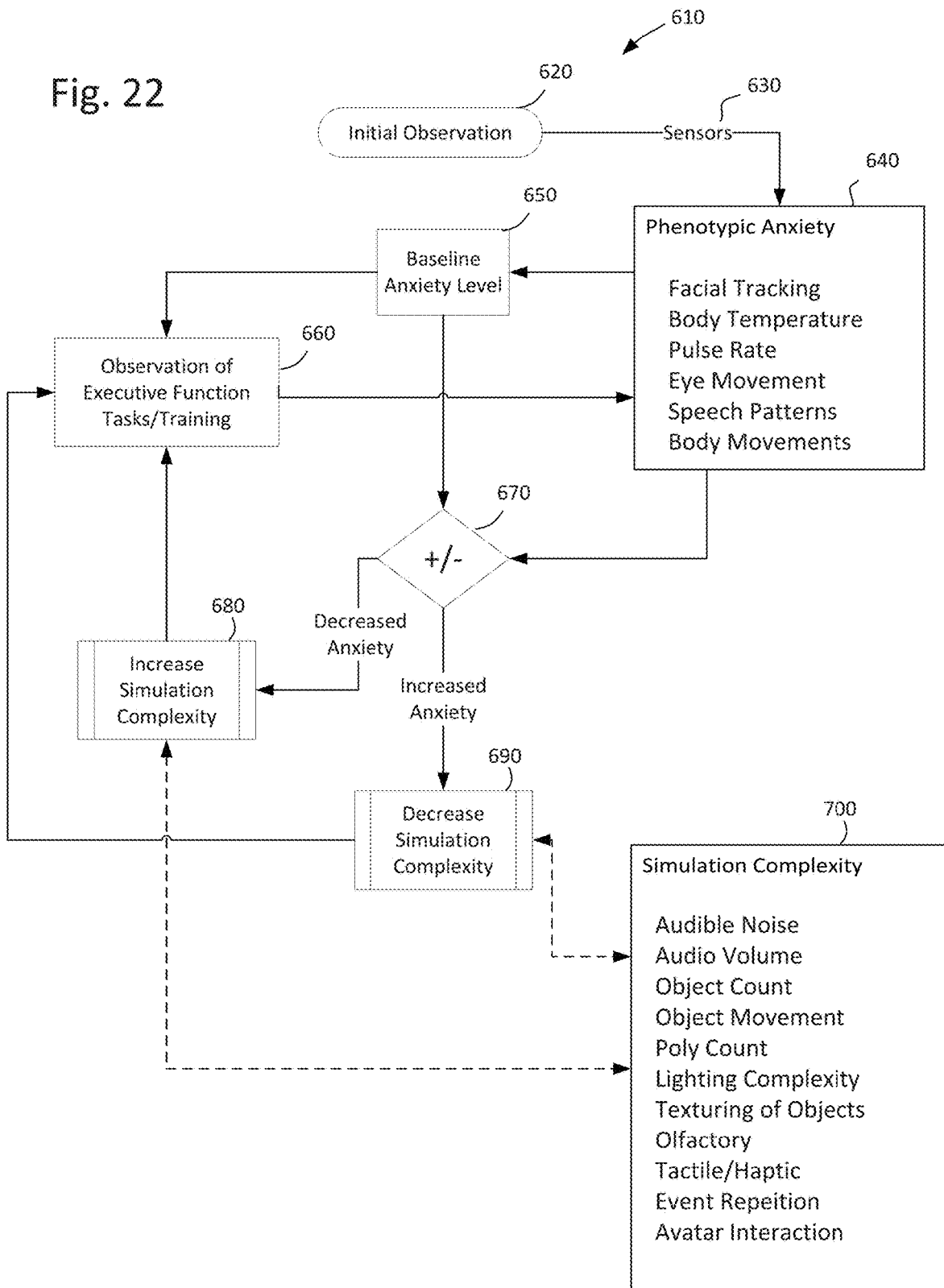
FIG. 22 is a flow chart showing the variation in simulation complexity responsive to real-time monitoring of subject anxiety levels.

FIG. 22 shows a process according to an embodiment of the invention denoted as 610 as a whole. Initial observation 620 of subject 20 by sensors 630 derive a baseline anxiety level 650 from phenotypic anxiety attributes 640. The session begins and the system observes the tasks and/or training to develop executive functions 660. The phenotypic anxiety 640 is continually measured during the session. Increasing anxiety levels of subject 20 automatically causes computer simulation to decrease in complexity 690 by changing simulation features 700. Decreasing anxiety levels of subject 20 enables the computer simulation to reintroduce simulation complexity 680, which is intended to develop the subject's ability to perform executive functions in real-world conditions.

Embodiments of the invention may be applied to numerous anxiety-intense environments such as a computer-simulated environment of an aircraft cabin for the treatment of flight anxiety. The computer may activate movement in a chair in which the subject sits to simulate air turbulence. The subject's pulse rapidly increases and his ability to continue through the therapeutic session is in jeopardy. The computer automatically determines the subject needs a more calming environment. However, rather than simply terminate the turbulence simulation, the AI-driven avatar offers pre-recorded calming words to the subject that they are safe, and the ride will soon smooth out.

An embodiment of the present invention is a virtual, mixed, and/or augmented reality environment for the patient Several key components are adaptable under the invention:

Environment: For example, the experience can take place in a home, classroom, work or outdoor environment.

Display: The experiences can be delivered on a wide variety of display types. These currently include laptop, large screen TV, full wall projection, and full surround as enabled by a CAVE (Cave Automatic Virtual Environment), a VR (Virtual Reality), an AR (Augmented Reality) or MR (Mixed Reality) headset.

Virtual or Mixed: The experience can be purely virtual or can blend virtual objects with the physical setting. Purely virtual experiences are common, but we can include the real setting as part of the experience. Clearly, if a headset is used, the blending of the real and virtual can be done with a variety of existing and evolving technologies and algorithms (e.g., HoloLens or Magic Leap or Vive Pro).

Number of Avatars in Environment: The virtual environment can have one or even many avatars.

Diversity of Avatars: The avatars that populate the environment can be of varying ages, ethnicities, and behavioral/cultural/family situation profiles.

Ability to Capture, Analyze and Adapt: The system includes capabilities to capture "performances" and to support annotations by subject-matter experts. The system automates much of the analysis and adds the ability to adapt the experience in real-time, based on these analyses.

Annotations describing a participant's affective states can be used in reflective learning. The invention supports this activity by focusing on capturing, analyzing and identifying nonverbal cues during cyberlearning experiences. These cues can then be offered to subject-matter experts in support of their providing annotations (semi-automated) or can be used to directly specify annotations without human intervention (automated). Challenges that one encounters here in both body gestures and facial expressions include self-occlusion. A particular example of this in facial expressions is hand-to-face occlusion (common with children with ASD). The present invention includes synthesized versions of these occlusions that are used to train a deep learning system to identify expressions in the context of hidden landmarks.

In addition to dealing with self-occlusion, the present invention includes a novel machine learning approach to explicitly disentangle facial expression representations from identity-related information. The disentangled facial expression representation can then be used to identify emotional responses or even to impose these same emotional responses on avatars, using the unique characteristics of each avatar.

Glossary of Claim Terms

Anxiety means a nervous condition characterized by a state of excessive uneasiness and apprehension.

Augmented Reality means technologies that superimpose a computer-generated image on a user's view of the real world, thus providing a composite view.

Autism Spectrum Disorder (ASD) is a developmental disorder that affects communication and behavior. Autism is known as a "spectrum" disorder because there is wide variation in the type and severity of symptoms people experience.

Avatar means an icon or figure representing a particular character in a computer simulation. For the purposes of this specification, the avatar is an automated, computer-controlled object rendered it the computer-simulated environment representing a human or other animals (e.g., canine).

Baseline means the starting anxiety level prior to, or at the time the computer simulation is initiated. Baseline levels may be obtained under moderate to low environmental stimulation but should be consistently measured under the same conditions between therapeutic sessions.

Executive functioning (EF) means brain processes that include (but are not necessarily limited to) inhibition, memory, attention, flexibility, planning, and problem-solving.

Haptic means perception and manipulation of objects using the senses of touch and proprioception.

Head Mounted Display (HMD) is a digital display device worn on the head or integrated into a helmet A HMD may present a completely virtual reality environment or may also reflect projected images wherein a user may see through it in augmented reality environments. Some commercially available HMDs include those sold under the brands' OCULUS RIFT and MICROSOFT HOLOLENS.

Mixed Reality means the combination of virtual and real worlds to generate new environments and visualizations wherein physical and digital objects co-exist and interact in real-time.

Olfactory means relating to the sense of smell.

Phenotypic anxiety level means observable displays of anxiety detectable by quantified, sensor-implemented monitoring of an individual.

Sensor means a device that detects or measures a physical property and records or conveys its value. In the case of the present invention, a sensor monitors visual, audio, temperature, and other physical properties of a human subject.

Sensory overload is when one or more of the body's senses experiences in an individual experiences and overload that causes stress or anxiety in the person.

Tactile means of or connected with the sense of touch.

UV mapping means the 3D modeling process of projecting a 2D image to a 3D model's surface for texture mapping.

Virtual Environment means the audio, visual, tactile, and other sensory features of a computer-generated simulation.

Virtual Reality means a computer-generated simulation of a three-dimensional image or environment that can be interacted with in a seemingly real or physical way by a person using special electronic equipment, such as a helmet with a screen inside or gloves fitted with sensors.

The advantages set forth above, and those made apparent from the foregoing description, are efficiently attained. Since certain changes may be made in the above construction without departing from the scope of the invention, itis intended that allmatters contained in the foregoing description or shown in the accompanying drawings shall be interpreted as illustrative and not in a limiting sense.

What is claimed is:

1. An apparatus for providing therapy for Autism Spectrum Disorder (ASD), the apparatus comprising:

a control module comprising a computer processor communicatively coupled to a simulation data store, the simulation data store having machine-readable values for computer-generated features in a computer-simulated environment in which a human subject with ASD is immersed, the computer-generated features include visual objects;

a rendering module communicatively coupled to the control module; the rendering module generates the visual objects in the computer-simulated environment;

a visual display device communicatively coupled to the rendering module, the visual display device displaying the visual objects in the computer-simulated environment;

an array of sensory variables accessible by the rendering module, the sensory variables quantifying an amount of visual information generated by the rendering module and presented in the computer-simulated environment, the sensory variables selected from the group consisting of polygon count of rendered objects in the environment, lighting complexity of the environment, texture complexity of rendered objects in the environment and rendered frames-per-second;

a sensing module communicatively coupled to the control module and at least one or more digital sensors, the sensing module receiving data from the digital sensors indicative of a physiological parameter of the human subject and quantifying a real-time sensory load value of the human subject from the data indicative of the physiological parameter, the real-time sensory load value readable by the control module;

a sensory load threshold datastore communicatively coupled to the control module, the sensory load threshold datastore storing an upper sensory load state value constant, the sensory load threshold datastore also storing a lower sensory load state value constant;

a sensory load threshold function operable on the control module, the sensory load threshold function receiving the real-time sensory load value of the human subject, the upper sensory load value constant and the lower sensory load value constant whereby the sensory load threshold function returns a low result responsive to the real-time sensory load value of the human subject being less than the lower sensory load value; a high result responsive to the real-time sensory load value of the human subject being greater than the upper sensory load value; and an inbounds result responsive to the real-time sensory load value of the human subject being above the lower sensory load value and less than the upper sensory load value;

whereby responsive to a low result returned from the sensory load threshold function, the control module instructs the rendering module to increase the values of the sensory variables to thereby increase the amount of visual information generated by the rendering module and presented within the computer-simulated environment;

responsive to a high result returned from the sensory load threshold function, the control module instructs the rendering module to decrease the values of the sensory variables to thereby decrease the amount of visual information generated by the rendering module and presented within the computer-simulated environment; and responsive to an inbounds result returned from the sensory load threshold function, the control module instructs the rendering module to maintain substantially the same values of the sensory variables to thereby sustain the same amount of visual information generated by the rendering module and presented within the computer-simulated environment.

2. The apparatus of claim 1 wherein the physiological parameter detectable by the at least one or more sensors is selected from the group consisting of facial tracking, body movement, body temperature, pulse rate, respiratory rate, eye movement, and speech patterns.

3. The apparatus of claim 1 wherein the visual display device is selected from the group consisting of single panel display monitors, multi-panel display monitors, rear projection displays, front projection displays, head-mounted virtual reality displays, and head-mounted augmented reality displays.

4. The apparatus of claim 1 further comprising an audio processing unit (APU) communicatively coupled to the rendering module, the APU generates an audio output in the computer-simulated environment.

5. The apparatus of claim 1 wherein the digital sensors are selected from the group consisting of cameras, radar, thermometers, heart rate monitor, pulse-oximeters, and microphones.

6. The apparatus of claim 1 wherein the rendering module generates a computer-generated simulation selected from the group consisting of a classroom, a workplace, a vehicle, a battlefield, a hospital and an athletic event.

7. The apparatus of claim 1 wherein human subject is tested on executive functions within computer-simulated environment whereby the apparatus provides benefit in improving executive function skills.

8. The apparatus of claim 1 wherein the computer-simulated environment is selected from the group consisting of a doctor's visit, asking out a peer on a date, and asking for help in a situation.

9. An apparatus for providing therapy for Autism Spectrum Disorder (ASD), the apparatus comprising:

a control module comprising a computer processor communicatively coupled to a simulation data store, the simulation data store having machine-readable values for computer-generated features in a computer-simulated environment in which a human subject is immersed, the computer-generated features include an audio output;

a rendering module communicatively coupled to the control module; the rendering module generates the audio output in the computer-simulated environment;

an audio output device communicatively coupled to the rendering module, the audio output device broadcasting the audio output in the computer-simulated environment;

an array of audio track variables accessible by the rendering module, the audio track variables quantifying an amount of audio information generated by the rendering module and presented in the computer-simulated environment;

a sensing module communicatively coupled to the control module and at least one or more digital sensors, the sensing module receiving data from the digital sensors indicative of a physiological parameter of the human subject and quantifying a real-time sensory load value of the human subject from the data indicative of the physiological parameter, the real-time sensory load value readable by the control module;

a sensory load threshold datastore communicatively coupled to the control module, the sensory load threshold datastore storing an upper sensory load state value constant, the sensory load threshold datastore also storing a lower sensory load state value constant;

a sensory load threshold function operable on the control module, the sensory load threshold function receiving the real-time sensory load value of the human subject, the upper sensory load value constant and the lower sensory load value constant whereby the sensory load threshold function returns a low result responsive to the real-time sensory load value of the human subject being less than the lower sensory load value; a high result responsive to the real-time sensory load value of the human subject being greater than the upper sensory load value; and an inbounds result responsive to the real- time sensory load value of the human subject being above the lower sensory load value and less than the upper sensory load value;

whereby responsive to a low result returned from the sensory load threshold function, the control module instructs the rendering module to increase the values of the audio track variables to thereby increase the amount of audible information generated by the rendering module and presented within the computer-simulated environment;

responsive to a high result returned from the sensory load threshold function, the control module instructs the rendering module to decrease the values of the sensory variables to thereby decrease the amount of audible information generated by the rendering module and presented within the computer-simulated environment; and responsive to an inbounds result returned from the sensory load threshold function, the control module instructs the rendering module to maintain substantially the same values of the sensory variables to thereby sustain the same amount of audible information generated by the rendering module and presented within the computer-simulated environment.

10. The apparatus of claim 9 wherein the audio track variables are selected from the group consisting of background noise, background dialog, foreground dialog and foreground noise.

11. The apparatus of claim 9 wherein the audio track variables include broadcast interval.

12. The apparatus of claim 9 wherein the physiological parameter detectable by the at least one or more sensors is selected from the group consisting of facial tracking, body movement, body temperature, pulse rate, respiratory rate, eye movement, and speech patterns.

13. The apparatus of claim 9 further comprising an audio processing unit (APU) communicatively coupled to the rendering module, the APU generates an audio output in the computer-simulated environment.

14. The apparatus of claim 9 wherein the digital sensors are selected from the group consisting of cameras, radar, thermometers, heart rate monitor, pulse-oximeters, and microphones.

15. The apparatus of claim 9 wherein human subject is tested on executive functions within computer-simulated environment whereby the apparatus provides benefit in improving executive function skills.

16. An apparatus for providing therapy for Autism Spectrum Disorder (ASD), the apparatus comprising:
a control module comprising a computer processor communicatively coupled to a simulation data store, the simulation data store having machine-readable values for computer-generated features in a computer-simulated environment in which a human subject is immersed, the computer-generated features include visual objects and an audio output;
a rendering module communicatively coupled to the control module; the rendering module generates the visual objects in the computer- simulated environment;
a visual display device communicatively coupled to the rendering module, the visual display device displaying the visual objects in the computer-simulated environment;
an array of sensory variables accessible by the rendering module, the sensory variables quantifying an amount of visual information generated by the rendering module and presented in the computer-simulated environment, the sensory variables selected from the group consisting of polygon count of rendered objects in the environment, lighting complexity of the environment, texture complexity of rendered objects in the environment and rendered frames-per-second;
a sensing module communicatively coupled to the control module and at least one or more digital sensors, the sensing module receiving data from the digital sensors indicative of the human subject's pulse rate and quantifying a real-time sensory load value of the human subject from the pulse rate, the real-time sensory load value readable by the control module;
a sensory load threshold datastore communicatively coupled to the control module, the sensory load threshold datastore storing an upper sensory load state value constant, the sensory load threshold datastore also storing a lower sensory load state value constant;
a sensory load threshold function operable on the control module, the sensory load threshold function receiving the real-time sensory load value of the human subject, the upper sensory load value constant and the lower sensory load value constant whereby the sensory load threshold function returns a low result responsive to the real-time sensory load value of the human subject being less than the lower sensory load value; a high result responsive to the real-time sensory load value of the human subject being greater than the upper sensory load value; and an inbounds result responsive to the real- time sensory load value of the human subject being above the lower sensory load value and less than the upper sensory load value;
whereby responsive to a low result returned from the sensory load threshold function, the control module instructs the rendering module to increase the values of the sensory variables to thereby increase the amount of visual information generated by the rendering module and presented within the computer-simulated environment;
responsive to a high result returned from the sensory load threshold function, the control module instructs the rendering module to decrease the values of the sensory variables to thereby decrease the amount of visual information generated by the rendering module and presented within the computer-simulated environment; and responsive to an inbounds result returned from the sensory load threshold function, the control module instructs the rendering module to maintain substantially the same values of the sensory variables to thereby sustain the same amount of visual information generated by the rendering module and presented within the computer-simulated environment.

17. The apparatus of claim 16 wherein the visual display device is selected from the group consisting of single panel display monitors, multi-panel display monitors, rear projection displays, front projection displays, head-mounted virtual reality displays, and head-mounted augmented reality displays.

18. The apparatus of claim 16 further comprising an audio processing unit (APU) communicatively coupled to the rendering module, the APU generates an audio output in the computer-simulated environment.

19. The apparatus of claim 16 wherein the digital sensors are selected from the group consisting of cameras, radar, thermometers, heart rate monitor, pulse- oximeters, and microphones.

20. The apparatus of claim 16 wherein human subject is tested on executive functions within computer-simulated environment whereby the apparatus provides benefit in improving executive function skills.

* * * * *